(12) United States Patent
Oh et al.

(10) Patent No.: US 9,671,482 B2
(45) Date of Patent: Jun. 6, 2017

(54) METHOD OF OBTAINING IMAGE AND PROVIDING INFORMATION ON SCREEN OF MAGNETIC RESONANCE IMAGING APPARATUS, AND APPARATUS THEREOF

(71) Applicant: SAMSUNG ELECTRONICS CO., LTD., Suwon-si (KR)

(72) Inventors: Keum-yong Oh, Yongin-si (KR); Jun-ki Lee, Suwon-si (KR); Se-tae Kim, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 13/920,523

(22) Filed: Jun. 18, 2013

(65) Prior Publication Data

US 2014/0111199 A1    Apr. 24, 2014

(30) Foreign Application Priority Data

Oct. 18, 2012 (KR) .................. 10-2012-0116072
Feb. 19, 2013 (KR) .................. 10-2013-0017661

(51) Int. Cl.
| | | |
|---|---|---|
| G01R 33/565 | (2006.01) | |
| A61B 5/00 | (2006.01) | |
| A61B 5/055 | (2006.01) | |
| A61B 5/11 | (2006.01) | |
| G01R 33/54 | (2006.01) | |

(52) U.S. Cl.
CPC ........ G01R 33/56509 (2013.01); A61B 5/055 (2013.01); A61B 5/11 (2013.01); A61B 5/7207 (2013.01); A61B 5/7221 (2013.01); G01R 33/546 (2013.01); A61B 5/721 (2013.01)

(58) Field of Classification Search
CPC .............. G01R 33/5676; G01R 33/546; G01R 33/56509; A61B 5/055; A61B 5/11; A61B 5/1127; A61B 5/7207; A61B 5/721
USPC .................................................. 324/307–309
See application file for complete search history.

(56) References Cited

U.S. PATENT DOCUMENTS

| | | | |
|---|---|---|---|
| 5,427,101 A | 6/1995 | Sachs et al. | |
| 6,407,548 B1 * | 6/2002 | Dietz ............................ | 324/307 |
| 6,690,965 B1 * | 2/2004 | Riaziat et al. ................ | 600/428 |
| 6,937,696 B1 * | 8/2005 | Mostafavi ........................ | 378/95 |
| 7,663,369 B2 | 2/2010 | Kassai | |
| 8,488,856 B2 | 7/2013 | Yui | |

(Continued)

FOREIGN PATENT DOCUMENTS

| | | |
|---|---|---|
| CN | 101238978 A | 8/2008 |
| CN | 101415365 A | 4/2009 |

(Continued)

OTHER PUBLICATIONS

Anne, "The science behind the MRI image." Date published: May 9, 2012. Date viewed: Sep. 3, 2014. Whole Page. <http://mri-info.net/welcome/?attachment_id=677>.*

(Continued)

Primary Examiner — Melissa Koval
Assistant Examiner — Rishi Patel
(74) Attorney, Agent, or Firm — Sughrue Mion, PLLC

(57) ABSTRACT

An MRI method includes detecting movement of an object while a protocol is executed to capture an image of a region of the object, and outputting information indicating occurrence of the movement, based on a value of a movement amount.

32 Claims, 18 Drawing Sheets

(56) References Cited

U.S. PATENT DOCUMENTS

| | | | |
|---|---|---|---|
| 8,688,193 B2 | 4/2014 | Doyle et al. | |
| 2002/0026115 A1* | 2/2002 | Nehrke et al. | 600/410 |
| 2003/0195413 A1* | 10/2003 | Rubin et al. | 600/411 |
| 2004/0012390 A1* | 1/2004 | Stoyle | 324/307 |
| 2005/0107685 A1 | 5/2005 | Seeber | |
| 2006/0182362 A1 | 8/2006 | McLain et al. | |
| 2007/0205769 A1* | 9/2007 | Yui et al. | 324/318 |
| 2008/0186027 A1 | 8/2008 | Kassai | |
| 2008/0211497 A1* | 9/2008 | Iwadate et al. | 324/307 |
| 2008/0309333 A1* | 12/2008 | Stehning et al. | 324/307 |
| 2009/0092305 A1* | 4/2009 | Ditt et al. | 382/131 |
| 2009/0326367 A1 | 12/2009 | Doyle et al. | |
| 2010/0087729 A1* | 4/2010 | Takizawa et al. | 600/413 |
| 2010/0199207 A1 | 8/2010 | Hopf et al. | |
| 2010/0213937 A1* | 8/2010 | Nagao et al. | 324/309 |
| 2011/0150309 A1* | 6/2011 | Barfett et al. | 382/131 |
| 2011/0230755 A1 | 9/2011 | MacFarlane et al. | |
| 2012/0045107 A1 | 2/2012 | Matsuda et al. | |
| 2012/0235679 A1* | 9/2012 | Xue | G01R 33/56509 324/307 |
| 2012/0243756 A1 | 9/2012 | Samsonov et al. | |
| 2012/0257806 A1* | 10/2012 | Sheltraw et al. | 382/131 |
| 2013/0023753 A1* | 1/2013 | Kawamura | A61B 5/055 600/410 |
| 2013/0310655 A1* | 11/2013 | Sachs et al. | 600/301 |
| 2014/0024924 A1* | 1/2014 | Goto et al. | 600/413 |

FOREIGN PATENT DOCUMENTS

| | | |
|---|---|---|
| JP | 04-246334 A | 9/1992 |
| JP | 10-295669 A | 11/1998 |
| JP | 2004-208954 A | 7/2004 |
| JP | 2007-61545 A | 3/2007 |
| JP | 2008-212626 A | 9/2008 |
| JP | 2008-212634 A | 9/2008 |
| JP | 2009-279238 A | 12/2009 |
| JP | 2010-22690 A | 2/2010 |
| KR | 10-2010-0002148 A | 1/2010 |

OTHER PUBLICATIONS

"How to Guide: Fix Windows Update Error 80070539 on Windows 7." Date Published: Aug. 14, 2011. Date viewed: Sep. 4, 2014. Tee Support Blog. <http://blog.teesupport.com/how-to-guide-fix-windows-update-error-80070539-on-windows-7/>.*

Written Opinion dated Sep. 27, 2013, issued by the International Searching Authority in counterpart International Application No. PCT/KR2013/005845.

International Search Report dated Sep. 27, 2013, issued by the International Searching Authority in counterpart International Application No. PCT/KR2013/005845.

Tobias Kober et al., "Head Motion Detection Using FID Navigators", Magnetic Resonance in Medicine, Feb. 17, 2011, pp. 135-143, XP055078827, vol. 66, No. 1.

Elisabeth C. Caparelli et al., "k-Space based summary motion detection for functional magnetic resonance imaging", NeuroImage, Oct. 1, 2003, p. 1411 to 1418, XP055078826, vol. 20, No. 2.

Theodore R. Steger et al., "Real-time motion detection of functional MRI data", Journal of Applied Clinical Medical Physics, Apr. 1, 2004, pp. 64-70, XP055078823, vol. 5, No. 2.

Communication dated Sep. 20, 2013, issued by the European Patent Office in counterpart European Application No. 13174675.2.

Communication dated Mar. 26, 2014, issued by the Korean Intellectual Property Office in counterpart Korean Application No. 10-2013-0017661.

Communication from the Japanese Patent Office dated Sep. 24, 2014, in a counterpart Japanese application No. 2013-155358.

Communication dated Sep. 24, 2014 issued by Japanese Patent Office in counterpart Japanese Patent Application No. 2013-155358.

Communication dated May 26, 2015, issued by the State Intellectual Property Office of the People's Republic of China in counterpart Chinese Application No. 201310355776.0.

Communication dated Apr. 14, 2015 issued by the European Patent Office in counterpart European Patent Application No. 13174675.2.

* cited by examiner

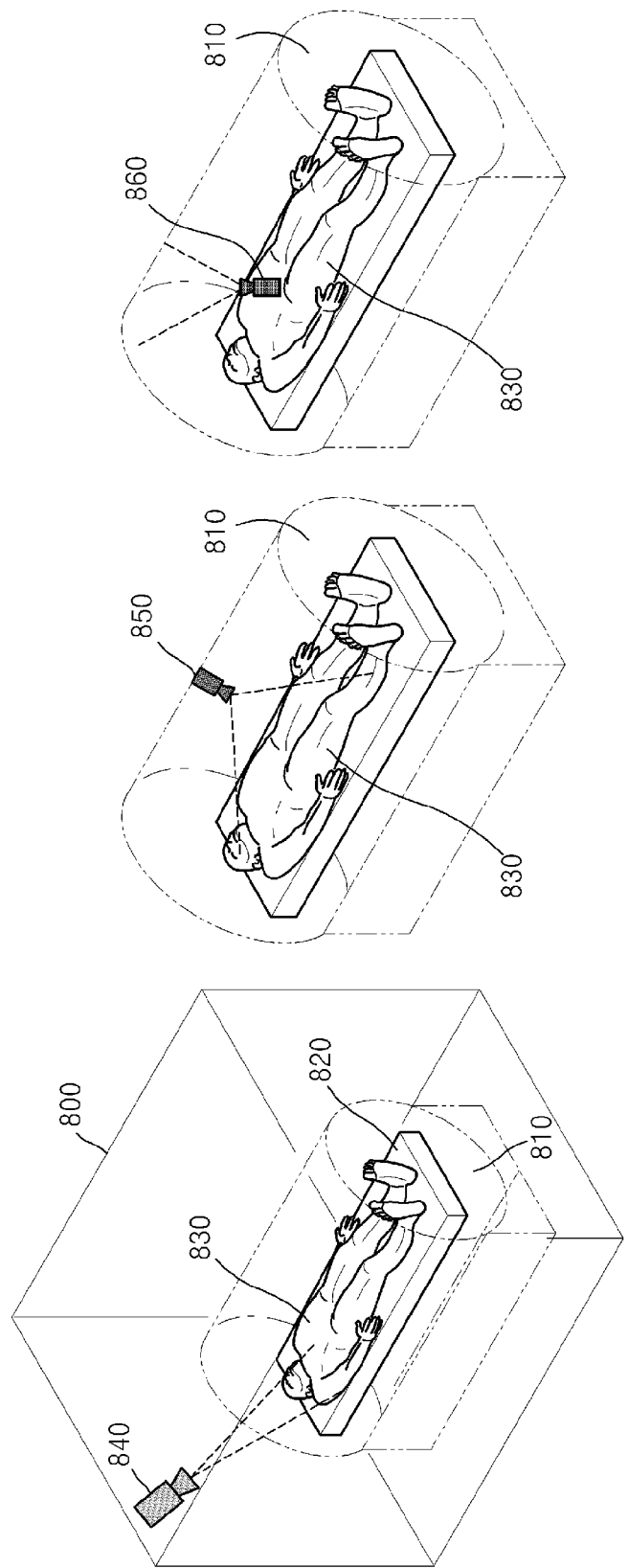

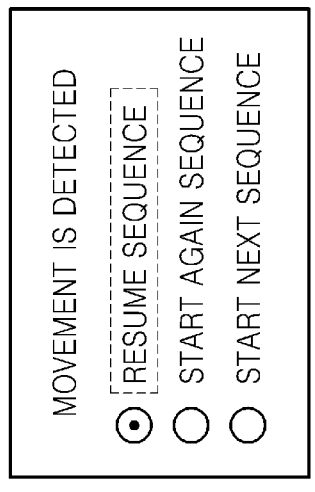
FIG. 11A
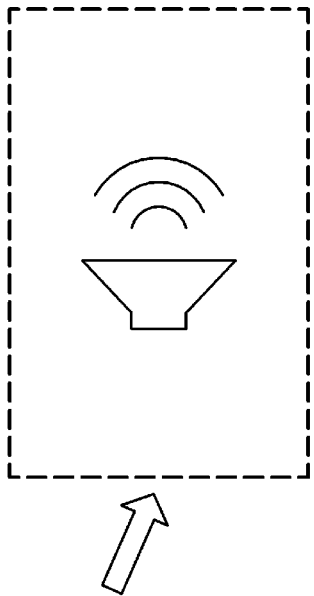
FIG. 11B
FIG. 11C

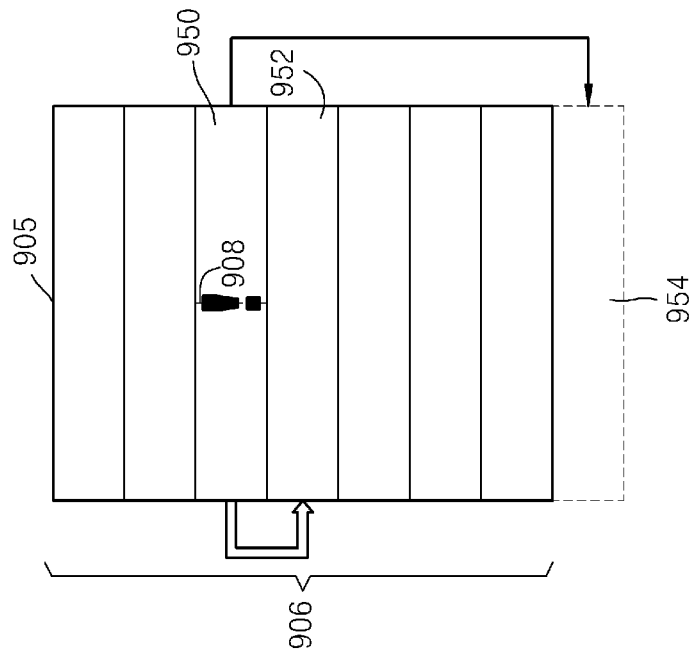
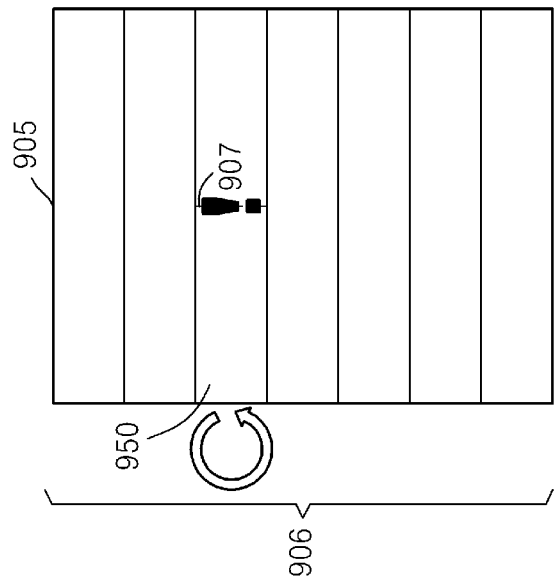

FIG. 14A

| 1 | Preview scan | |
|---|---|---|
| 2 | t2_haste_tra_8mm free br | 00:29 |
| 3 | t1_fl2d_tra_mbh | 00:37 |
| 4 | t1_fl2d_fs_tra_mbh | 00:40 |
| 5 | t2_tse_tra_mbh | 00:29 |
| 6 | T1_fl2d_tra_mbh | 00:44 |
| 7 | t2_haste_tra_8mm free br | 00:44 |
| 8 | t2_haste_tra_8mm br | |

| 2 | t2_haste_tra_8mm free br | 00:37 |
|---|---|---|
| 4 | t1_fl2d_fs_tra_mbh | 00:29 |
| 6 | T1_fl2d_tra_mbh | |

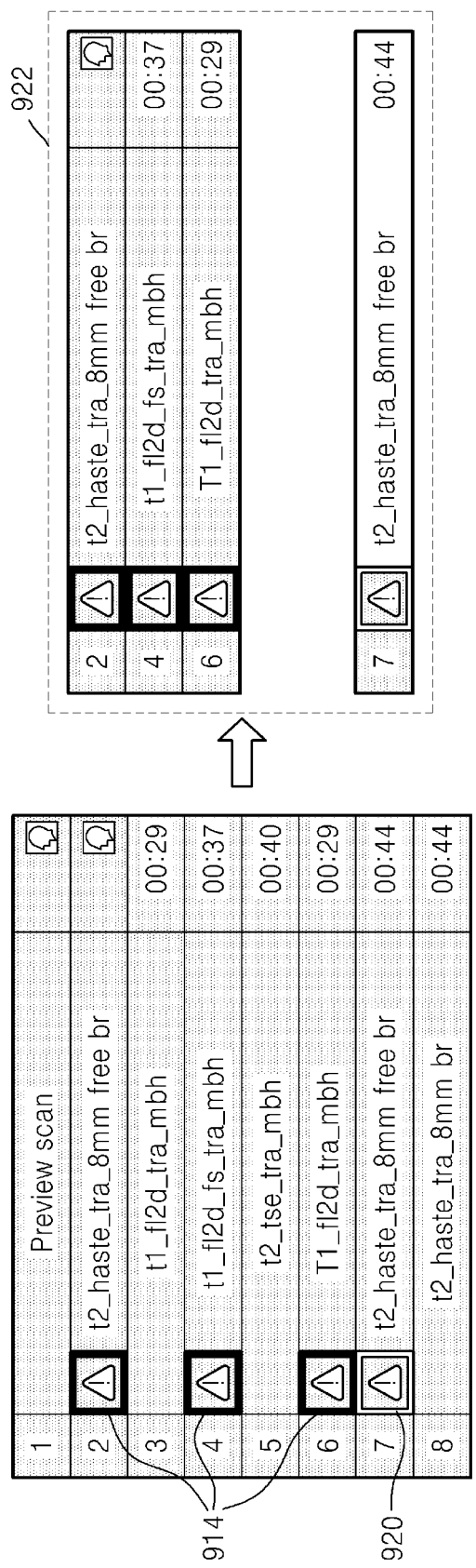

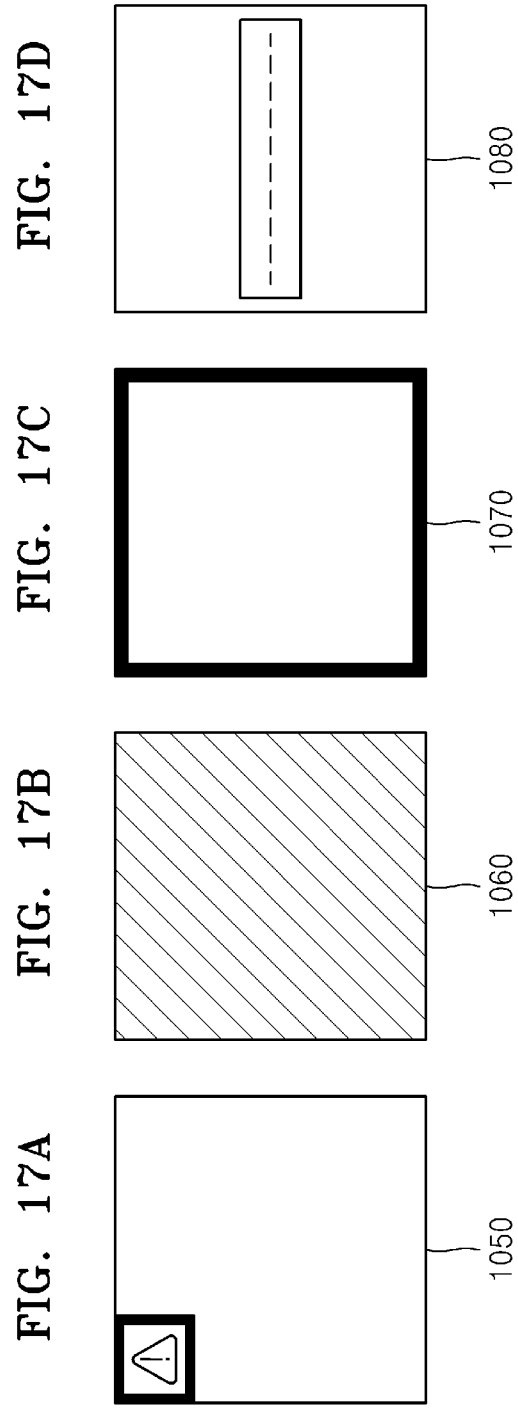

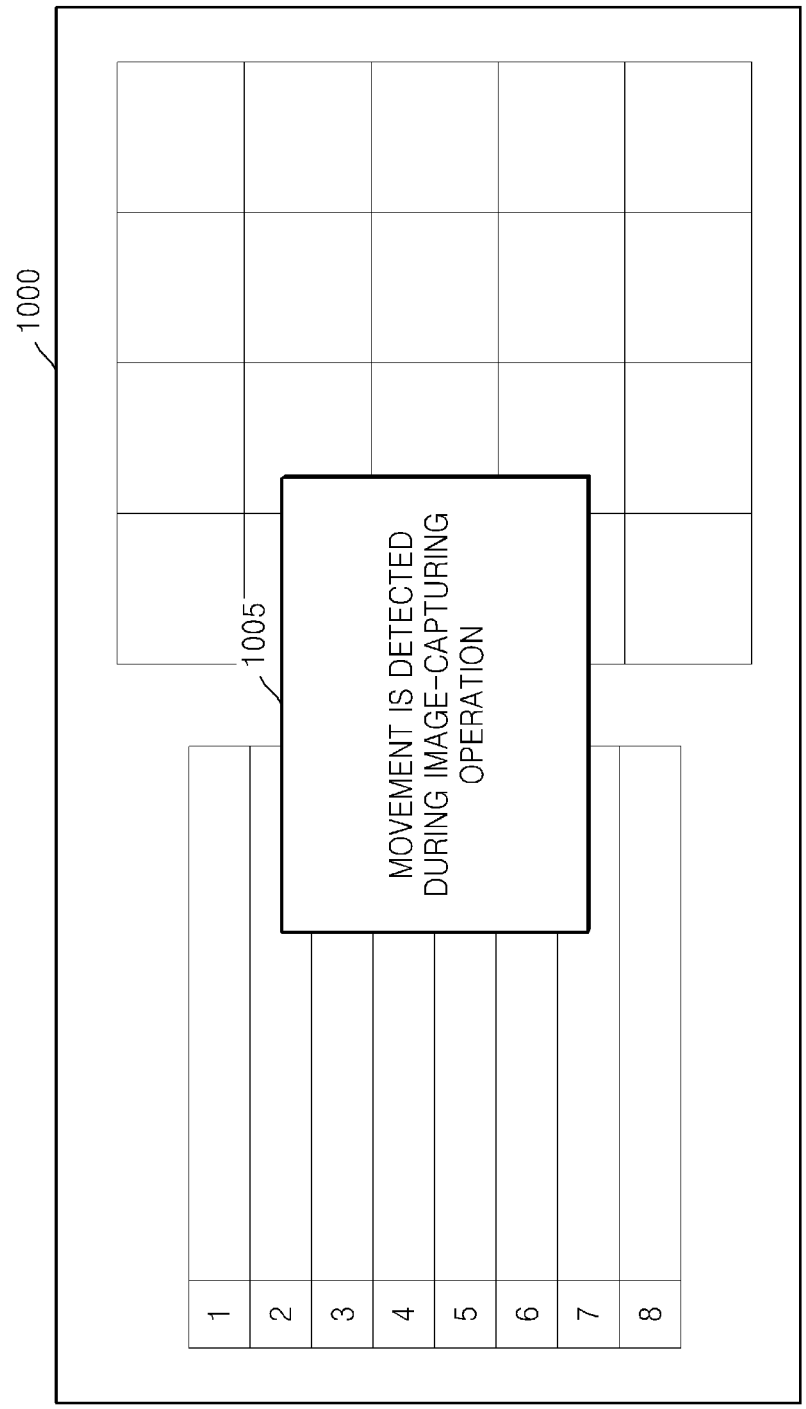

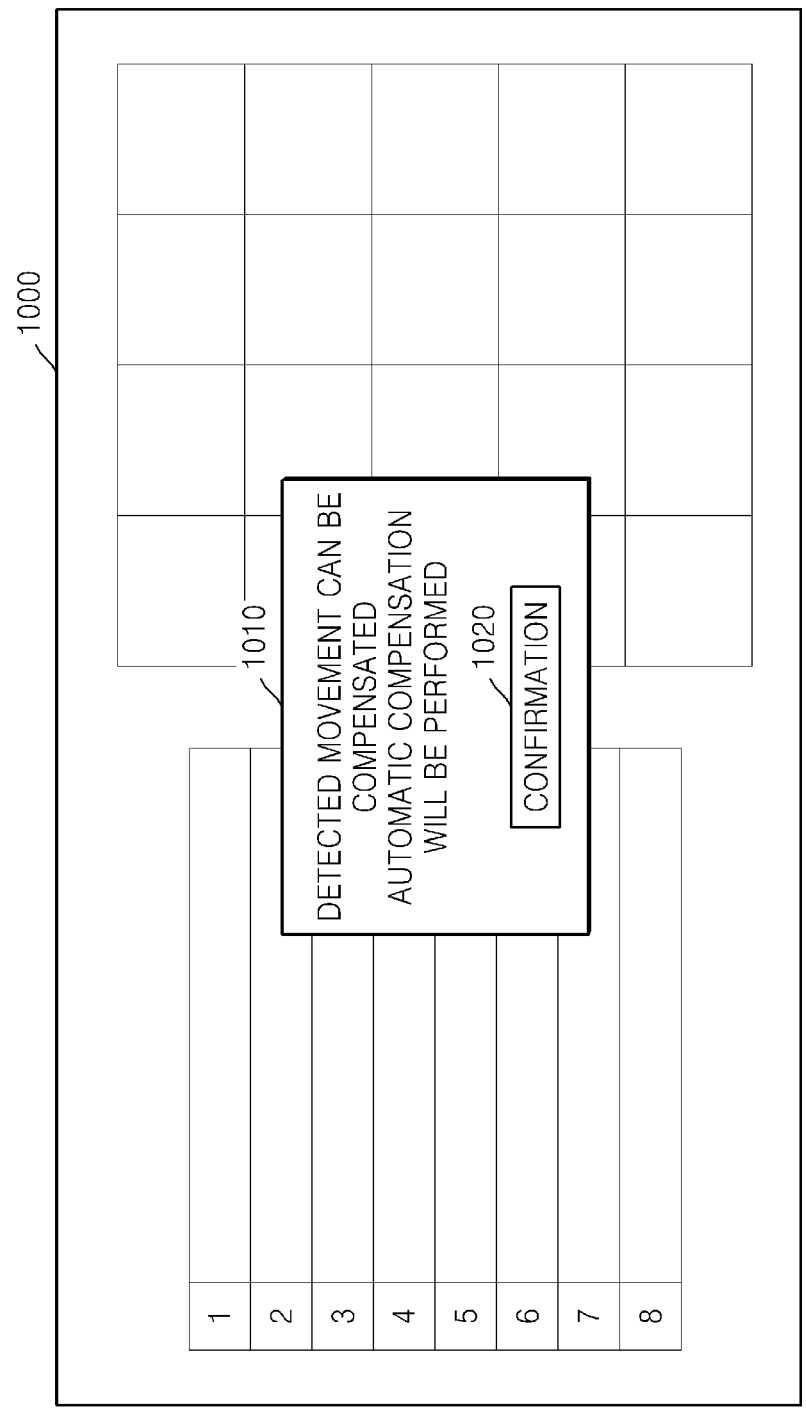

METHOD OF OBTAINING IMAGE AND PROVIDING INFORMATION ON SCREEN OF MAGNETIC RESONANCE IMAGING APPARATUS, AND APPARATUS THEREOF

CROSS-REFERENCE TO RELATED PATENT APPLICATIONS

This application claims priority from Korean Patent Application No. 10-2012-0116072, filed on Oct. 18, 2012, and Korean Patent Application No. 10-2013-0017661, filed on Feb. 19, 2013, in the Korean Intellectual Property Office, the disclosures of which are incorporated herein in their entireties by reference.

BACKGROUND

1. Field

Apparatuses and methods consistent with exemplary embodiments relate to obtaining an image and providing information on a screen, and more particularly, to a protocol control by a magnetic resonance imaging (MRI) apparatus to obtain an image of an object.

2. Description of the Related Art

Magnetic resonance imaging (MRI) obtains imaging information by exposing nuclei to a magnetic field and then resonating the nuclei. When a particular high frequency is incident on a nucleus that has been magnetized by an external magnetic field, the nucleus in a low energy state absorbs high frequency energy and then is excited to a high energy state, and this is called the resonance of the nucleus. Different nuclei have different resonance frequencies, and resonance is affected by an intensity of the external magnetic field. Countless nuclei are present in the human body, and, for example, hydrogen nuclei are used in the MRI.

An MRI apparatus is advantageous in that the MRI apparatus is noninvasive, exhibits an excellent tissue contrast, as compared to a computerized tomography (CT) apparatus, and does not have artifacts due to the bone tissue. Also, since the MRI apparatus can capture various cross-sectional images in various directions without moving an object, the MRI apparatus is widely used with other imaging apparatuses.

However, movement of an object, which occurs while an MR image is obtained, forms a motion artifact in the MR image. The motion artifact is shown as bright noise in the MR image or as an extraneous shape having repeating densities. In particular, the motion artifact frequently occurs while capturing an image of a patient who repeatedly moves or an image of a child. A radiation technician using a related art MRI apparatus cannot instantly determine a presence of a motion artifact that occurs due to the movement of an object while an MR image is captured. That is, only after a user of the related art MRI apparatus generates the MR image, via a pulse sequence applied to a predetermined region of the object, the user checks the MR image for presence of a motion artifact and then the pulse sequence is executed again.

SUMMARY

Exemplary embodiments may address at least the above problems and/or disadvantages and other disadvantages not described above. Also, exemplary embodiments are not required to overcome the disadvantages described above, and an exemplary embodiment may not overcome any of the problems described above.

One or more of exemplary embodiments provide a method of automatically controlling a process of a protocol and/or a pulse sequence according to movement of an object which is detected during an image-capturing operation, whereby a motion artifact in an MR image is minimized.

Furthermore, since the movement of the object is detected, a user of an MRI apparatus may easily identify a pulse sequence and an image which need to be examined by the user for the motion artifacts.

According to an aspect of an exemplary embodiment, there is provided a method of providing information, the method performed by an MRI apparatus and includes detecting movement of an object while a protocol proceeds to capture an image of a predetermined region of the object; and outputting information indicating occurrence of the movement, based on whether a level of the movement is equal to or greater than a preset threshold value.

The outputting may include outputting a notice message indicating the information, by using at least one of graphical data, text data, and audio data.

When the level of the movement is equal to or greater than the threshold value, the outputting may include displaying a first marker indicating that the movement is detected.

The displaying may include displaying the first marker on at least one of a region in which information corresponding to a pulse sequence in which the movement is detected is displayed, and an MR image obtained via the pulse sequence in which the movement is detected, wherein the pulse sequence is from among one or more pulse sequences included in the protocol.

When the protocol is ended, the method may further include extracting pulse sequences in which the movement is detected from among one or more pulse sequences included in the protocol; and displaying a list of the pulse sequences on a screen of the MRI apparatus.

The extracting may include extracting pulse sequences in which a value of the movement is equal to or greater than the threshold value.

The extracting may include extracting pulse sequences that display a first marker indicating that the movement is detected.

The displaying may include differently displaying a pulse sequence in which the detected movement is equal to or greater than the threshold value, and a pulse sequence in which the detected movement is less than the threshold value.

The method may further include proceeding with the extracted pulse sequences after the protocol is ended.

The method may further include proceeding with the extracted pulse sequences, based on a user input.

The detecting may include detecting the movement by comparing MR images that are obtained via a pulse sequence in which the movement is detected from among pulse sequences included in the protocol.

The comparing may include comparing a reference MR image with a currently obtained MR image of the pulse sequence in which the movement is detected.

The comparing may include comparing a currently obtained MR image with a previous MR image of the pulse sequence in which the movement is detected.

The detecting the movement may include comparing a plurality of the predetermined regions on the MR images.

The detecting the movement may include comparing image characteristic values of the MR images.

The detecting may include observing the object by using a camera attached to at least one of a bore of the MRI apparatus, a radio frequency (RF) coil, and the object.

The detecting may include detecting the movement by using at least one of a pressure sensor, an optical sensor, a tilt sensor, an acceleration sensor, a gyro sensor, and a magnetic field sensor.

The method may further include suspending the protocol, based on whether the level of the movement is equal to or greater than the threshold value.

The method may further include resuming the suspended protocol, when the level of the movement is changed to a level that is equal to or less than the threshold value, or when a user input is received.

The resuming may include resuming a pulse sequence from a start, wherein the movement is detected in the pulse sequence from among pulse sequences included in the protocol.

The resuming may include resuming a pulse sequence from a point at which MRI data is completely obtained via the image-capturing, wherein the movement is detected in the pulse sequence from among pulse sequences included in the protocol.

The resuming may include resuming a pulse sequence from a point at which generation of an MR image via the image-capturing is completed, wherein the movement is detected in the pulse sequence from among pulse sequences included in the protocol.

The resuming may include resuming a pulse sequence from a point at the protocol is suspended due to detection of the movement, wherein the movement is detected in the pulse sequence from among pulse sequences included in the protocol.

The resuming may include resuming a next pulse sequence of a pulse sequence in which the movement is detected from among pulse sequences included in the protocol.

The method may further include, when the level of the movement is less than the threshold value, compensating an MR image that is obtained via a pulse sequence in which the movement is detected from among one or more pulse sequences included in the protocol.

The outputting may include displaying a second marker indicating that the MR image is compensated.

The displaying may include displaying the second marker on at least one of a region in which information corresponding to a pulse sequence in which the movement is detected is displayed, and an MR image obtained via the pulse sequence in which the movement is detected.

According to another aspect of an exemplary embodiment, there is provided an MRI apparatus for providing information, the MRI apparatus including a protocol manager for proceeding with a protocol to capture an image of a predetermined region of an object; a sensor for detecting movement of the object while the protocol proceeds; and an output device for outputting information indicating occurrence of the movement, based on whether a level of the movement is equal to or greater than a preset threshold value.

According to another aspect of an exemplary embodiment, there is provided a computer-readable recording medium having recorded thereon a program for executing the method.

According to another aspect of an exemplary embodiment, there is provided a method of providing information, the method performed by an MRI apparatus and includes detecting movement of an object while a protocol to capture an image of a predetermined region of the object proceeds; when a level of the movement is equal to or greater than a preset threshold value, outputting information indicating occurrence of the movement by displaying a marker indicating that the movement is detected; when the level of the movement is less than the preset threshold value, compensating an MR image that is obtained via a pulse sequence in which the movement is detected from among one or more pulse sequences included in the protocol; when the protocol is ended, extracting the pulse sequence in which the movement is detected from among the one or more pulse sequences included in the protocol; and proceeding with the extracted pulse sequence after the protocol is ended.

BRIEF DESCRIPTION OF THE DRAWINGS

The above and/or other aspects will become more apparent by describing in certain exemplary embodiments, with reference to the accompanying drawings, in which:

FIGS. 10A, 10B, and 10C illustrate examples of detecting movement of an object, according to exemplary embodiments;

FIGS. 11A, 11B, and 11C illustrate a method of displaying a marker indicating movement of an object, according to an exemplary embodiment;

FIGS. 13A and 13B illustrate an example of resuming a suspended pulse sequence, according to an exemplary embodiment;

FIGS. 14A and 14B illustrate an example of outputting a list of suspended pulse sequences, according to an exemplary embodiment;

FIGS. 15A and 15B illustrate an example of separately outputting a list of suspended pulse sequences and a list of pulse sequences in which MR images are compensated, according to an exemplary embodiment;

FIGS. 17A, 17B, 17C, and 17D illustrate examples of a marker displayed on a screen, according to an exemplary embodiment;

FIG. 18 illustrates an example of outputting information indicating detection of movement of an object, according to an exemplary embodiment; and FIG. 19 illustrates an example of outputting a notice message about a process of a protocol, in response to movement of an object, according to an exemplary embodiment.

DETAILED DESCRIPTION

Figure 1:
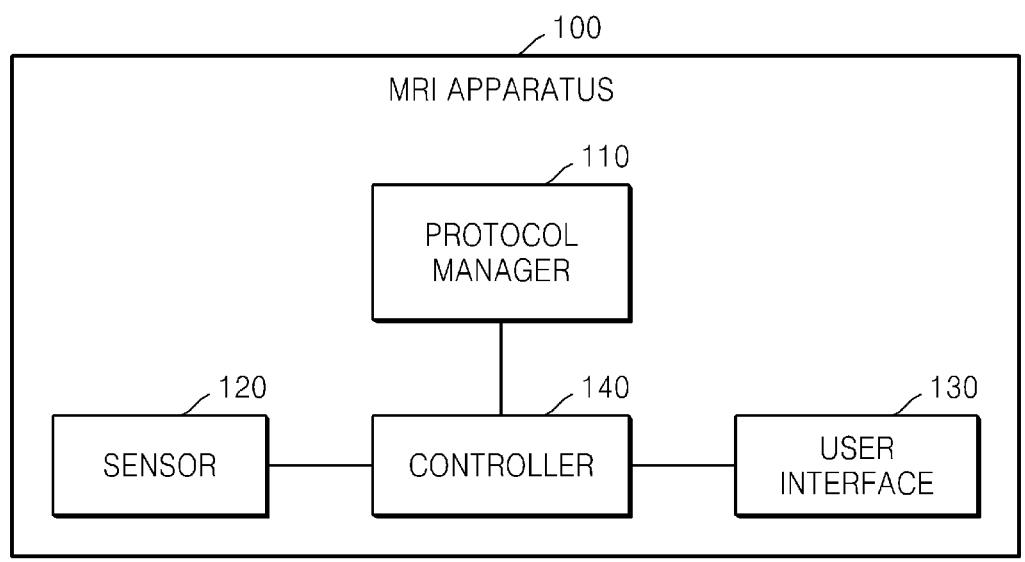
FIG. 1 is a block diagram illustrating a structure of an MRI apparatus according to an exemplary embodiment.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

All terms including descriptive or technical terms which are used herein should be construed as having meanings that are obvious to one of ordinary skill in the art. However, the terms may have different meanings according to an intention of one of ordinary skill in the art, precedent cases, or the appearance of new technologies. Also, some terms may be arbitrarily selected by the applicant, and in this case, the meaning of the selected terms is described in detail below. Thus, the terms used herein have to be defined based on the meaning of the terms together with the description throughout the specification.

Also, when a part "includes" or "comprises" an element, unless there is a particular description contrary thereto, the part can further include other elements, not excluding the other elements. Terms such as "unit" and "module" indicate a unit for processing at least one function or operation, wherein the unit and the block may be embodied as hardware or software or embodied by combining hardware and software.

As used herein, the term "and/or" includes any and all combinations of one or more of the associated listed items.

Expressions such as "at least one of," when preceding a list of elements, modify the entire list of elements and do not modify the individual elements of the list.

FIG. 1 is a block diagram illustrating a structure of an MRI apparatus 100 according to an exemplary embodiment. The MRI apparatus 100 may include a protocol manager 110, a sensor 120, a user interface 130, and a controller 140. However, the MRI apparatus 100 may further include other structural elements in addition to the components shown in FIG. 1.

The MRI apparatus 100 obtains an MR signal from an object in a magnet system, thereby generating an MR image. The object on a cradle is moved to an inside of the magnet system. The magnet system may include a bore, a shim coil, a gradient coil, and a radio frequency (RF) coil.

The magnet system is placed in a shield room that shields an external RF signal, and a user, i.e., a radiation technician who uses the MRI apparatus 100, may control the magnet system in a separate operating room. The user may diagnose the object via the MR image displayed on a screen of the MRI apparatus 100.

Furthermore, the obtained MR image may be stored in an internal server of a hospital, for example, or in an external server via a picture archiving and communication system, and the MRI apparatus 100 may store the MR image according to the Digital Imaging and Communications in Medicine (DICOM) standard. The MRI apparatus 100 may store the MR image in a storage unit (not shown) included in the MRI apparatus 100.

A protocol and a pulse sequence included in the protocol are described in detail below. The pulse sequence indicates a predetermined RF signal output from the magnet system to obtain the MR signal from the object. For example, a magnetic field is applied to capture an image of a predetermined region of the object, and then an RF signal is transmitted to the object. The pulse sequence may indicate the RF signal having a pre-defined order, time, and pattern according to a target region and a direction.

The protocol includes one or more pulse sequences, and is divided according to regions of the object. For example, the protocol may include region protocols including a head protocol, a neck protocol, a waist protocol, or the like, and each of the region protocols may include one or more pulse sequences. For example, the head protocol may include a pulse sequence to obtain a scout image, a pulse sequence to obtain an axial view image that is a horizontal-axis cross-section of the object, and a pulse sequence to obtain a T1 emphasis image for an anatomical examination. However, the head protocol may further include various types of pulse sequences in addition to the aforementioned sequences.

The protocol manager 110 manages a process of a protocol to capture an image of the object. For example, the protocol manager 110 may start a protocol to capture an image of a predetermined region of the object, may suspend an ongoing protocol, or may resume a suspended protocol. When an external input signal to select a region to be captured is received from the user of the MRI apparatus 100 as an input, the protocol manager 110 may determine a protocol with respect to the region to be captured and may proceed with the protocol.

The protocol manager 110 may obtain information about a pulse sequence included in the protocol. As described above, since the protocol includes one or more protocols, the protocol manager 110 may obtain information about a pulse sequence included in the protocol with respect to the region to be captured. Accordingly, the protocol manager 110 may control the process of the pulse sequence included in the protocol. In more detail, the protocol manager 110 may control the process of the pulse sequence included in the protocol, so that the protocol manager 110 may start, suspend, or resume the pulse sequence.

The protocol manager 110 may control a process of the protocol (i.e., the process of the pulse sequence) according to predetermined criteria. For example, the protocol manager 110 may suspend the protocol when movement of the object is detected, or may suspend the protocol when a level of the detected movement is equal to or greater than a predetermined threshold value. Alternatively, when the level of the detected movement changes to be equal to or less than a predetermined threshold value, or when an external input signal is received, the protocol manager 110 may resume the suspended protocol. These operations are described below with reference to FIGS. 2 through 5 in more detail.

The protocol manager 110 may sequentially proceed with the one or more pulse sequences included in the protocol, or may select some pulse sequences and may proceed with the selected pulse sequences. For example, the protocol manager 110 may extract at least one pulse sequence from the pulse sequences included in the protocol according to a criteria or an external input signal, and may proceed with the extracted pulse sequence. Alternatively, the protocol manager 110 may determine an order and a list of pulse sequences for a capturing operation, and may sequentially proceed with the determined pulse sequences.

The sensor 120 detects movement of the object. For example, the sensor 120 may detect the movement of the object on a cradle while the MR image is captured (i.e., while the protocol proceeds).

The sensor 120 may include various types of sensors to detect the movement of the object. For example, the sensor 120 may include at least one of an optical sensor such as an infrared sensor that is arranged in a bore, a tilt sensor or a pressure sensor for detecting a change in a position or a pressure of the object on a cradle, a frequency sensor for using frequency data of the received RF signal, and an image sensor for analyzing the MR image. In addition to the aforementioned sensors, the sensor 120 may further include various detecting means such as an acceleration sensor, a gyro sensor, a magnetic field sensor, or the like to detect the movement of the object.

The sensor 120 may detect the movement of the object according to the MR image. For example, the sensor 120 may obtain a difference value between image characteristic values by comparing a plurality of MR images obtained via the pulse sequence, and may determine occurrence of the movement when the difference value is equal to or greater than a threshold value.

In more detail, when the object moves during an image-capturing operation, a motion artifact may occur in the MR image, and the sensor 120 may compare a most-recently obtained MR image with other MR images among generated MR images. For example, the sensor 120 may compare a currently-obtained MR image with a reference MR image of an ongoing pulse sequence or may compare the currently-obtained MR image with an MR image that is previously obtained in the ongoing pulse sequence. The reference MR image may be an average image of the plurality of MR images obtained via the pulse sequence or may be an image that is selected by a user from the plurality of MR images obtained via the pulse sequence.

Accordingly, the sensor 120 may detect a blurring phenomenon by which a boundary of an object in the currently-obtained MR image is blurred or may detect a noise that occurs in the currently-obtained MR image. The sensor 120 may compare captured target areas of the object in the MR image or may compare changes in a vector direction of a captured target area.

For example, the sensor 120 may calculate the difference value by comparing the image characteristic value including brightness, chroma, resolution, a position of a boundary line, or the like of the MR image with image characteristic values of previous MR images, may determine occurrence of the motion artifact when the difference value is equal to or greater than the predetermined threshold value, and then may determine the occurrence of the movement by the object (i.e., the sensor 120 may detect the movement). However, when the difference value is less than the predetermined threshold value, the sensor 120 may determine that the movement is not substantial or non-existent.

The sensor 120 may detect the movement of the object by directly or indirectly observing the object by using an image-capturing device. For example, the sensor 120 may include various types of an image-capturing device such as an infrared-ray camera, a high-speed camera, a wide viewing angle camera, or the like, and may observe an object by using the image-capturing device.

The image-capturing device included in the sensor 120 may be arranged in a shield room in which the MRI apparatus 100 is positioned, may be arranged in the bore of the MRI apparatus 100, or may be directly attached to an RF coil and/or the object. The sensor 120 may analyze an image obtained by using the image-capturing device and then may detect whether the object moves while the protocol proceeds. The image-capturing device is described in greater detail below with reference to FIG. 10.

The sensor 120 may determine a threshold value with respect to a level of the movement. For example, the sensor 120 may determine the threshold value based on at least one of a function of the MRI apparatus 100, a type of the protocol, and a type of the pulse sequence included in the protocol. For example, the sensor 120 may determine a threshold value that varies in each of protocols, or may determine a threshold value for each of the pulse sequences.

The sensor 120 may compare a value of the level of the detected movement with a pre-determined threshold value. For example, to determine whether the movement of the object requires the ongoing protocol to be suspended, the sensor 120 may compare the value of the detected movement with the threshold value to determine whether the detected movement is equal to or greater than the threshold value, as described below with reference to FIGS. 2, 4, and 5 in more detail.

Also, when the sensor 120 detects the movement by comparing the MR images, the sensor 120 may set a threshold value having a reference value different from a reference value of a case of using the aforementioned sensor. For example, the threshold value may be changed according to in which manner the sensor 120 detects the movement of the object.

The user interface 130 provides the user with various types of information about an image-capturing operation with respect to the object, and receives an input to control the MRI apparatus 100 from the user. For example, the user interface 130 may provide the user with various types of information by outputting the MR image on the screen of the MRI apparatus 100, by displaying a marker on the output MR image, or by outputting a notice message in a graphical form or a text form to the user. In addition, the user interface unit 130 may output information about the ongoing protocol and pulse sequence to the screen and thus may provide the user with process information about a region that is being captured.

The user interface 130 may receive an external input signal from the user via various input means such as a mouse, a keyboard, a keypad, a touch pad, a touch screen, or the like. For example, the user interface 130 may receive a user input to control operations of the MRI apparatus 100, and for example, the user interface unit 130 may receive a user input to suspend or to resume the protocol and pulse sequence.

The controller 140 controls the operations of the MRI apparatus 100. For example, the controller 140 may control operations of the protocol manager 110, the sensor 120, and the user interface unit 130. For example, the controller 140 may control the protocol manager 110 to suspend the ongoing protocol, according to the movement of the object, which is detected by the sensor 120. The controller 140 may control the user interface unit 130 to output information about the protocol and pulse sequence, which are suspended by the protocol manager 110, to the screen.

Figure 2:
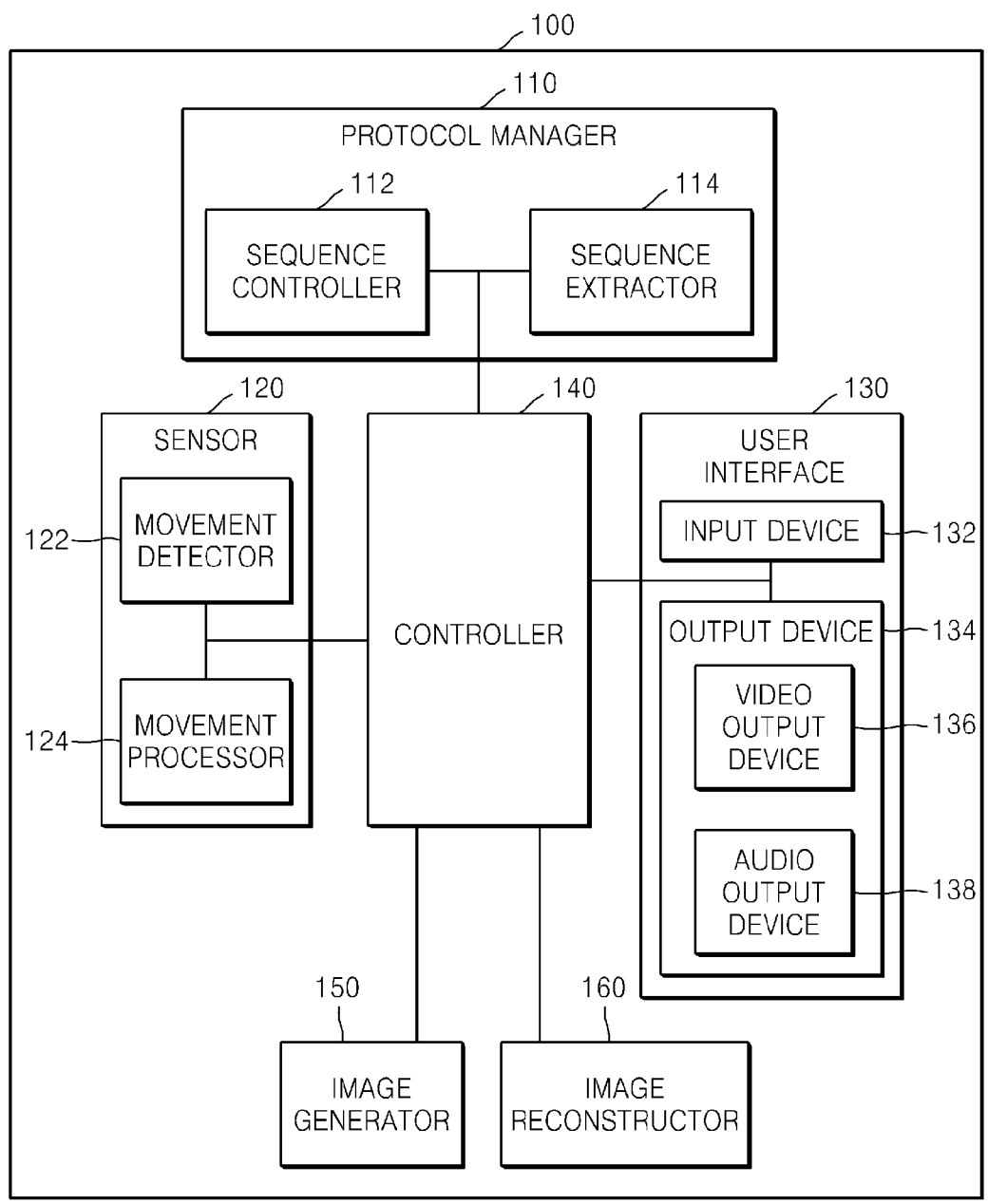
FIG. 2 a block diagram illustrating a structure of an MRI apparatus according to an exemplary embodiment.

FIG. 2 a block diagram illustrating a structure of an MRI apparatus 100 according to an exemplary embodiment. The MRI apparatus 100 of FIG. 2 further includes an image generator 150 and an image reconstructor 160, in addition to the protocol manager 110, the sensor 120, the user interface unit 130, and the controller 140 which are described with reference to FIG. 1. Hereinafter, the structure of the MRI apparatus 100 according to FIG. 2 is particularly described, and the features, which are the same as described above with reference to FIG. 1, are omitted.

The protocol manager 110 may include a sequence controller 112 and a sequence extractor 114. The sequence controller 112 controls a process of a protocol and one or more pulse sequences included in the protocol. For example, the sequence controller 112 may control each of the pulse sequences included in the protocol used to capture an image of an object and thus may start, suspend, or resume transmission of an RF signal.

An order and a list of the pulse sequences controlled by the sequence controller 112 may be determined by the protocol manager 110. For example, the protocol manager 110 may determine a protocol and one or more pulse sequences included in the protocol with respect to a target area of the object, and the sequence controller 112 may proceed with each of the pulse sequences included in the protocol. The order and the list of the pulse sequences controlled by the sequence controller 112 may be determined by the protocol manager 110 or by a user input.

The sequence extractor 114 extracts at least one pulse sequence from the pulse sequences included in the protocol. For example, the sequence extractor 114 may extract one or more pulse sequences from a plurality of pulse sequences according to a predetermined reference or an external input signal. A list of pulse sequences to be extracted by the sequence extractor 114 may include the plurality of pulse sequences or one pulse sequence, as described above. For example, pulse sequences extracted by the sequence extractor 114 and the number of extracted pulse sequences included in the protocol are not limited to the aforementioned feature. The sequence extractor 114 may extract one or more pulse sequences in response to a user input that is externally received via the user interface unit 130.

The sequence extractor 114 may extract the pulse sequences according to various types of references. For example, when movement of the object is detected while a protocol proceeds, the sequence extractor 114 may extract pulse sequences in which the movement of the object is detected. Alternatively, the sequence extractor 114 may extract only a pulse sequence whose value of the detected movement is equal to or greater than a threshold value, wherein the pulse sequence is from the pulse sequences in which the movement of the object is detected.

In another exemplary embodiment, the sequence extractor 114 may extract one or more pulse sequences based on markers displayed on a screen. For example, when the markers are displayed in the pulse sequences in which the movement of the object is detected, the sequence extractor 114 may extract the pulse sequences having the markers and separately generate a list of the pulse sequences. The sequence extractor 114 may extract a pulse sequence having a first marker indicating that a process is suspended and may extract a pulse sequence having a second marker indicating that an MR image is automatically compensated.

The sensor 120 may include a movement detector 122 and a movement processor 124. The movement detector 122 detects the movement of the object during an image-capturing operation. For example, the movement detector 122 may detect the movement of the object by using various methods, various types of sensors, or various types of image-capturing devices. The movement detector 122 may detect the movement by using one of the aforementioned sensors and the image-capturing devices or by using at least two of the aforementioned sensors and the image-capturing devices. The movement detector 122 may detect the movement by comparing at least two MR images.

The movement processor 124 determines a threshold value to control a process of a protocol according to the movement of the object. The movement processor 124 may compare the threshold value with a value of the movement of the object, which is detected by the movement detector 122.

In more detail, the object inevitably moves while an MR image is captured. For example, the object may slightly move involuntarily while the MR image is captured or may move due to a physical feature, an illness state, or an age (in particular, children) of the object, and this movement of the object may impede the image-capturing operation. If the amount of movement of the object, which is detected during an image-capturing operation, is slight, an affect with respect to the MR image may be disregarded. For example, the affect by the slight movement with respect to the MR image may be removed by compensating an image while the MR image is reconstructed via an obtained MR signal.

On the other hand, in a case where movement is detected so that it is problematic to diagnose the object by using an MR image (i.e., in a case where a motion artifact occurs), a new image in which the motion artifact is absent needs to be obtained.

Thus, in order to control a process of a protocol according to a value of the movement of the object, the movement processor 124 may determine a threshold value. For example, the movement processor 124 may determine whether to disregard the movement and to perform image compensation (i.e., whether to continue the protocol), or whether to suspend the protocol and resume an image-capturing operation after the movement of the object has ended, according to the threshold value.

The movement processor 124 may determine the threshold value, based on at least one of a function of the MRI apparatus 100, a type of the protocol, and types of one or more pulse sequences included in the protocol. For example, the movement processor 124 may determine the threshold value according to an image reconstruction function of the MRI apparatus 100, or may determine the threshold value according to a motion artifact occurrence possibility of the protocol and each of the pulse sequences included in the protocol.

In addition, the movement processor 124 may compare the value of the detected movement of the object with the threshold value. The value of the movement may vary depending on how the movement detector 122 detects the movement of the object.

For example, when the movement detector 122 measures the movement of the object by using a tilt sensor arranged in a cradle, the threshold value may correspond to an angle that is detected by the tilt sensor. For example, the movement processor 124 may compare the detected angle with a threshold angle, and as a result of the comparison, if the detected angle is greater than the threshold angle, the protocol manager 110 may suspend a process of the protocol. In more detail, for example, the movement processor 124 may determine a threshold angle as 1 degree, and may determine whether a tilt of the movement of the object is greater than 1 degree. On the other hand, if the detected angle is less than the threshold angle, the protocol manager 110 may continue the protocol and an MR image may be compensated during an image reconstruction operation.

The aforementioned example related to the angle of the tilt sensor is provided to describe the present exemplary embodiment, and references of the threshold value are not limited thereto. Also, while the example related to the angle of the tilt sensor is provided above, the movement detector 122 may detect the movement of the object by using various types of sensors, as described above with reference to FIG. 1.

For example, the movement processor 124 may compare the difference value between the image characteristic values of the MR images with a predetermined threshold value, and according to a result of the comparison, the movement processor 124 may determine whether the movement occurs.

The user interface 130 may include the input device 132 for receiving a user input and the output device 134 for providing various types of information to a user.

The input device 132 receives the user input to control the MRI apparatus 100. As described above with reference to FIG. 1, the input device 132 may receive the user input via various input means such as a mouse, a keyboard, a keypad, a touch pad, a touch screen, or the like. The user input received by the input device 132 may include a touch input via a part of the human body.

The output device 134 outputs an MR image that is obtained according to various types of information provided by the execution of the protocol, and provides the MR image to the user. The output device 134 may include a video output device 136 for outputting a video signal and an audio output device 138 for outputting an audio signal.

The video output device 136 may display and output various types of information processed by the MRI apparatus 100. For example, the video output device 136 may output various types of information related to an image-capturing operation of the object, and examples of the various types of information may include an MR image generated by processing an MRI signal, information about an ongoing protocol and one or more pulse sequences included in the protocol, a list of extracted pulse sequences, a mark indicating detection of movement, or the like. However, the examples of the various types of information which are output to a screen by the video output device 136 are exemplary, and in this regard, other types of information may be output to the screen.

In an exemplary embodiment, the video output device 136 may output a notice message with the information about the process of the protocol, which varies according to a value of the detected movement. The video output device 136 may output the notice message by using at least one of text data and graphical data.

When the video output device 136 is a touch screen, the video output device 136 may be an input means for receiving a touch input via a stylus pen or a part of the human body and may simultaneously be an output means for outputting information.

The video output device 136 may include at least one of a liquid crystal display (LCD), a thin-film transistor LCD (TFT LCD), an organic light-emitting diode (OLED) display, a flexible display, and a three-dimensional (3D) display. Also, in an exemplary embodiment, the MRI apparatus 100 may include two or more video output devices 136.

The audio output device 138 outputs information as an audio data to be provided to the user. For example, the audio output device 138 may output various types of information including a notice message indicating detection of movement, a message indicating a process or an end of the protocol, or the like. The audio output device 138 may output audio data by using an alarm sound or pre-stored audio data.

The image generator 150 captures an image of the object and thus obtains an MR signal. The image generator 150 may include a magnet system including a bore in which the object is positioned and a coil for applying a magnetic field and an RF signal to the object. The image generator 150 may apply the magnetic field to the object and may obtain the MR signal that is generated in response to the RF signal transmitted according to a predetermined pulse sequence.

The image reconstructor 160 generates an MR image. For example, the image reconstructor 160 may process the MR signal that is obtained by the image generator 150 and thus may generate the MR image. When the image reconstructor 160 generates the MR image, the image reconstructor 160 may compensate for a motion artifact that is equal to or less than a predetermined reference. For example, when the sensor 120 detects an amount of movement of the object, which has a value less than a pre-defined threshold value, the image reconstructor 160 may generate an MR image from which the motion artifact is removed. A result of the compensation by the image reconstructor 160 with respect to the MR image may vary according to an intensity of the magnetic field, a function of the MRI apparatus 100, types of pulse sequences, or the like.

A method of obtaining an MR image and providing information, performed by the MRI apparatus 100, is described below in detail with reference to FIGS. 3 through 8.

The flowcharts shown in FIGS. 3 through 8 include operations that are processed in chronological order by the MRI apparatus 100, the protocol manager 110, the sensor 120, the user interface unit 130, the controller 140, the image generator 150, and the image reconstructor 160 shown in FIGS. 1 and 2. Thus, hereinafter, although omitted, the descriptions of elements with respect to FIGS. 1 and 2 apply to the flowcharts of FIGS. 3 through 8.

Figure 3:
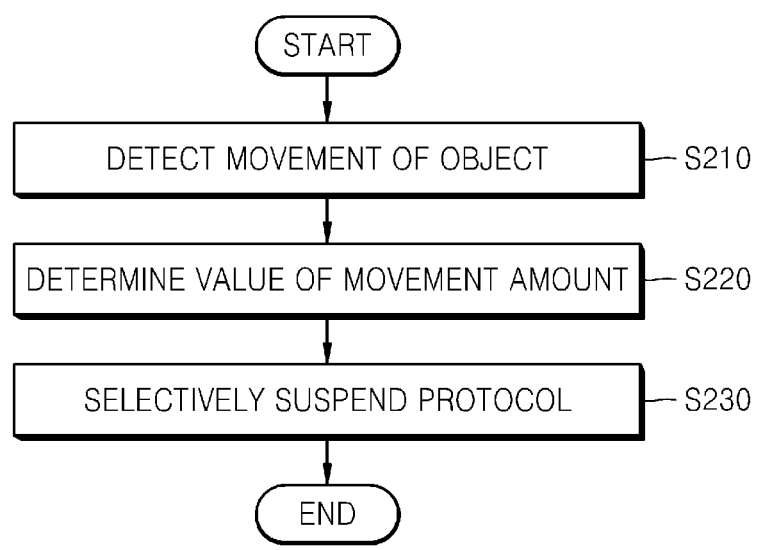
FIG. 3 is a flowchart of a method of obtaining an MR image, according to an exemplary embodiment.

FIG. 3 is a flowchart of a method of obtaining an MR image, according to an exemplary embodiment.

In operation S210, the MRI apparatus 100 detects movement of an object. For example, while one or more pulse sequences included in a protocol proceed, the MRI apparatus 100 detects the movement of the object. The MRI apparatus 100 may detect the movement of the object by using various types of sensors described above with reference to FIG. 1.

In operation S220, the MRI apparatus 100 determines a value of the movement amount of the object. For example, the MRI apparatus 100 may compare the value of the movement of the object with a pre-defined threshold value and then may determine whether the value is equal to or greater than the threshold value. As described above with reference to FIG. 1, the threshold value may be determined based on various references, and may vary according to an ongoing protocol and pulse sequences.

In operation S230, the MRI apparatus 100 selectively suspends the ongoing protocol. For example, based on a result of the determination in operation S220, the MRI apparatus 100 may suspend the ongoing protocol and pulse sequences. That the MRI apparatus 100 selectively suspends the ongoing protocol may mean that the MRI apparatus 100 continuously proceeds with the protocol or suspends the protocol, based on the result of the determination in operation S220. The selective suspension of the protocol, which is performed by the MRI apparatus 100, is described below in greater detail with reference to FIG. 4.

According to operations S210 through S230, the MRI apparatus 100 selectively suspends the protocol according to the movement of the object, which is detected during an image-capturing operation, so that it is possible to save time required to obtain and check an MR image and then to re-capture an MR image if the image contains noise. For example, when the MRI apparatus 100 detects the movement having a value equal to or greater than the threshold value, the MRI apparatus 100 suspends the protocol so that the occurrence of a motion artifact may be minimized.

Figure 4:
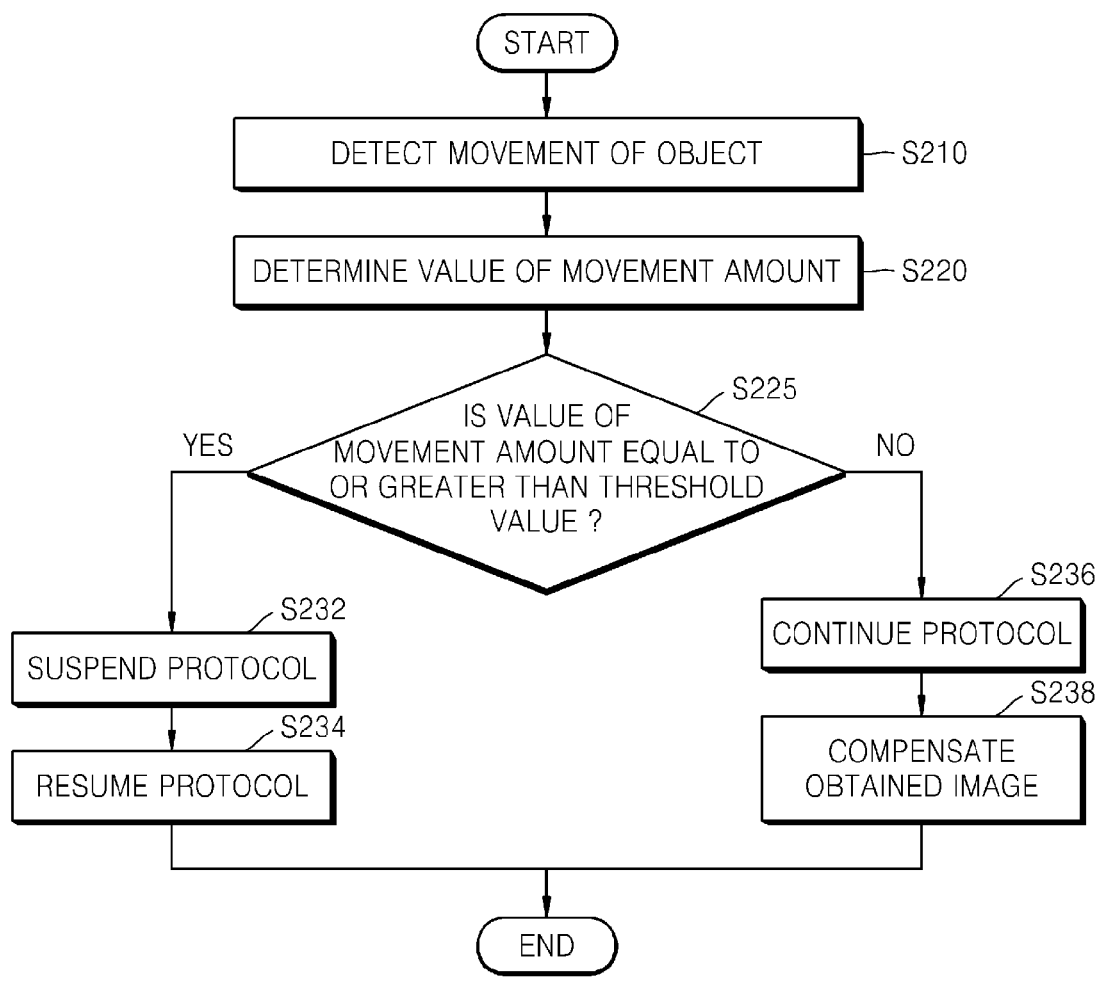
FIG. 4 is a flowchart of the method of obtaining an MR image, according to an exemplary embodiment.

FIG. 4 is a flowchart of the method of obtaining an MR image, according to an exemplary embodiment. The flowchart of FIG. 4 illustrates the flowchart of FIG. 3 in detail. Since operation S210 shown in the flowchart of FIG. 4 is the same as that in the flowchart of FIG. 3, detailed descriptions thereof are omitted here.

In operation S225, the MRI apparatus 100 determines whether the value of the detected movement is equal to or greater than the threshold value, based on a result of operation S220. When the value of the detected movement is equal to or greater than the threshold value, the MRI apparatus 100 proceeds to operation S236.

Otherwise, in operation S232, the MRI apparatus 100 suspends the ongoing protocol. In an exemplary embodiment, the MRI apparatus 100 suspends a pulse sequence of the protocol in which the movement is detected. For example, in operation S232, the MRI apparatus 100 suspends transmission of an RF signal and stands by until an additional input is received or a condition is satisfied.

In another exemplary embodiment, the MRI apparatus 100 does not suspend the ongoing pulse sequence in which the movement is detected, as described above. After the ongoing pulse sequence ends, the MRI apparatus 100 does not start the next pulse sequence which follows the pulse sequence in which the movement is detected and may stand by until the additional input is received or the condition is satisfied.

In operation S232, a procedure by which the MRI apparatus 100 suspends the protocol may be determined according to how the pulse sequence in which the movement is detected transmits the RF signal and/or how the pulse sequence in which the movement is detected collects data.

For example, when the RF signal is sequentially transmitted to predetermined areas in a regular direction (e.g., in a direction from a head of an object toward feet), the MRI apparatus 100 may suspend the pulse sequence in which the movement is detected. On the other hand, when the RF signal is transmitted to predetermined areas in an irregular direction (e.g., when the RF signal is transmitted to the discontinuous areas and then is transmitted to each gap between the predetermined areas), the MRI apparatus 100 may continue the ongoing sequence, but does not start the next pulse sequence.

In an exemplary embodiment, the MRI apparatus 100 may output information about the ongoing protocol and information about the ongoing pulse sequence to a screen. Accordingly, when the ongoing protocol is suspended in operation S232, the MRI apparatus 100 may display a first marker on a region of the screen which displays information about the pulse sequence in which the movement is detected. Accordingly, although the protocol is resumed in operation S234, a user of the MRI apparatus 100 may easily recognize which pulse sequence has been suspended. The display of a marker is described in detail below with reference to FIG. 9.

In operation S234, the MRI apparatus 100 resumes the protocol that has been suspended in operation S232. For example, the MRI apparatus 100 continues a process of transmitting again the RF signal and obtaining an MR signal, when an external input signal is received or a predetermined condition is satisfied, as described below with reference to FIG. 5 in more detail.

In operation S236, the MRI apparatus 100 continues the protocol. For example, when the value of the detected movement is less than the threshold value, an affect due to a motion artifact which affects the MR image is sufficiently small to be disregarded. Thus, the MRI apparatus 100 does not suspend the protocol. For example, when the object slightly and unintentionally moves, the MRI apparatus 100 does not suspend the protocol and continues an image-capturing operation.

In operation S238, the MRI apparatus 100 compensates the obtained MR image. When the value of the movement detected in operation S210 does not require re-capturing the MR image, the MRI apparatus 100 may obtain the MR image and may perform a post-processing, thereby compensating the MR image. The MRI apparatus 100 may compensate the MR image by using a motion correction algorithm. As described above with reference to FIG. 2, the MRI apparatus 100 may compensate the MR image while the MR signal is obtained and/or the MR image is reconstructed.

In another exemplary embodiment, the MRI apparatus 100 may display a second marker on a region of the screen of the MRI apparatus 100 which displays the information about the pulse sequence in which the movement is detected. The second marker may indicate that the movement is detected but is automatically compensated. The second marker may differ from the first marker described above in operation S232. The user of the MRI apparatus 100 may easily recognize that which pulse sequence has been suspended and an image of which a pulse sequence has been automatically compensated, via the first and second markers.

According to the features of the flowchart of FIG. 4, the MRI apparatus 100 may selectively determine whether to suspend the protocol according to the value of the detected movement. Accordingly, the MRI apparatus 100 does not suspend the protocol with respect to an MR image that does not require an image re-capturing operation, so that it is possible to save time required to determine that an MR image needs to be re-captured due to the occurrence of the motion artifact.

Figure 5:
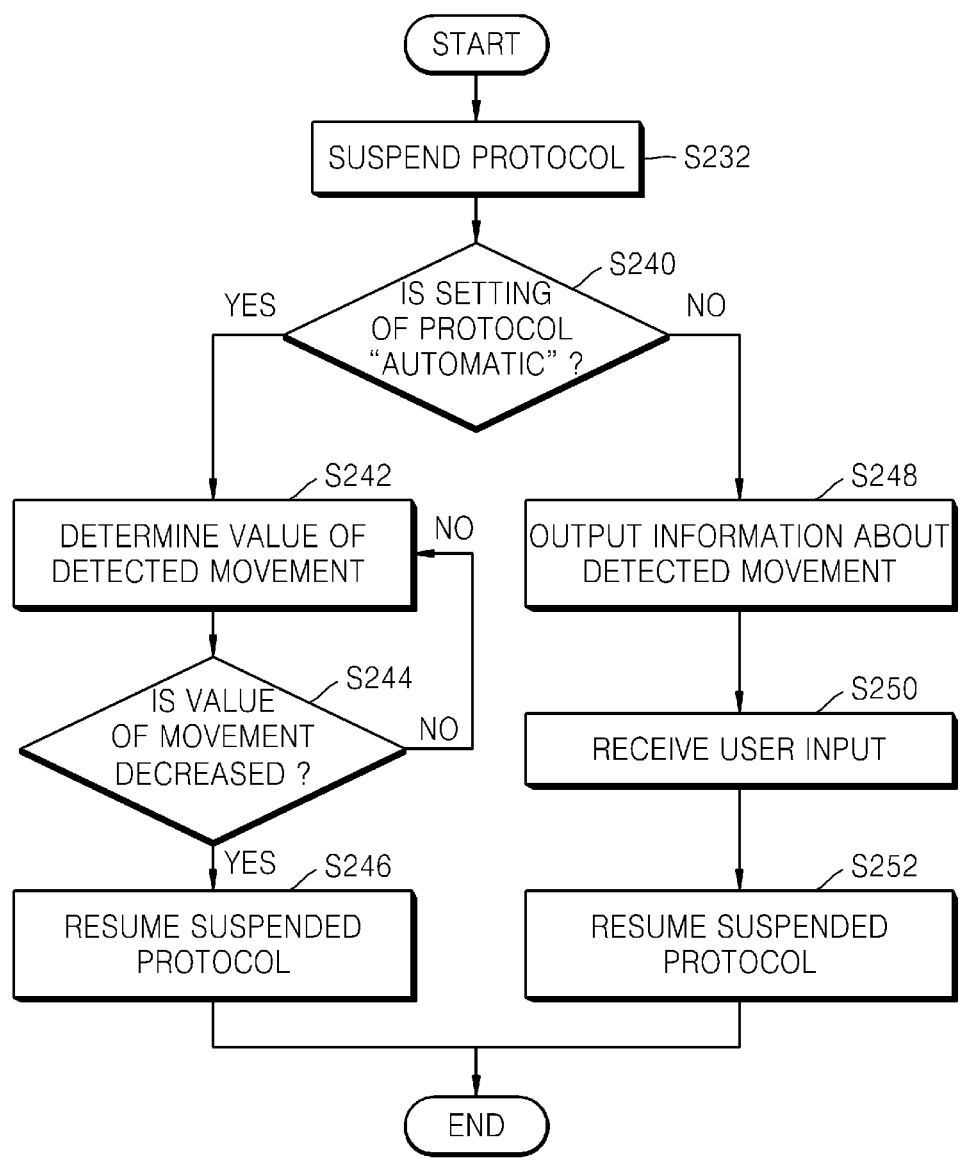
FIG. 5 is a flowchart of the method of obtaining an MR image, according to an exemplary embodiment.

FIG. 5 is a flowchart of the method of obtaining an MR image, according to an exemplary embodiment. The flowchart of FIG. 5 illustrates operation S234 of the flowchart of FIG. 4 in detail. Since operation S232 shown in the flowchart of FIG. 5 is the same as that in the flowchart of FIG. 4, detailed descriptions thereof are omitted here.

In operation S240, the MRI apparatus 100 checks setting of the protocol. For example, when the protocol is suspended in operation S232, the MRI apparatus 100 checks a predetermined setting value before the MRI apparatus 100 resumes the protocol. The MRI apparatus 100 may check whether the setting with respect to the resumption of the protocol is automatic or manual. When the protocol is automatically resumed, the MRI apparatus 100 proceeds to operation S242, and when the protocol is manually resumed, the MRI apparatus 100 proceeds to operation S248.

In operation S242, the MRI apparatus 100 continuously or periodically determines the value of the movement to determine whether the value of the movement, determined to be equal to or greater than the threshold value in operation S210, continues to be the same, increases, or decreases.

In operation S244, when the value of the detected movement is decreased to be equal to or less than a predetermined threshold value, the MRI apparatus 100 proceeds to operation S246, and when the value of the detected movement is not changed or increased, the MRI apparatus 100 returns to operation S242. The threshold value described in operation S244 may be equal to or different from the threshold value described in operation S225 of the flowchart of FIG. 4.

In operation S244, when the value of the movement is decreased to be equal to or less than the threshold value described in operation S225, the MRI apparatus 100 may proceed to operation S246. On the other hand, the MRI apparatus 100 may perform the determination based on a second threshold value indicating a value of movement which is smaller than the threshold value in operation S225.

In operation S246, the MRI apparatus 100 resumes the suspended protocol. For example, when a condition in operation S244 is satisfied, the MRI apparatus 100 automatically resumes the suspended protocol. Accordingly, in operations S242 through S246, the MRI apparatus 100 may automatically resume the suspended protocol, based on the value of the movement of the object.

In operation S248, the MRI apparatus 100 outputs information about the detected movement, which indicates that the protocol is suspended since the movement that is greater than the threshold value is detected, to the screen by using graphical data and/or text data, or may output audio data by using an alarm sound such as a beep sound.

Accordingly, when the information indicating that the protocol is suspended due to the movement of the object is output, the user of the MRI apparatus 100 may control the object not to move. For example, the user of the MRI apparatus 100 may deliver a message requesting the object not to move via a speaker of the magnet system.

In operation S250, the MRI apparatus 100 receives a user input with respect to the suspended protocol, and in this regard, the input may indicate resuming the protocol due to a removal of the movement of the object. The MRI apparatus 100 may receive the user input to resume the protocol via various types of inputs such as a touch input via a touch screen, an input via a keyboard, an input via a mouse, or the like.

In operation S252, the MRI apparatus 100 resumes the suspended protocol based on the user input received in operation S250. Accordingly, operations S248 through S252, the MRI apparatus 100 may manually resume the suspended protocol.

In operations S246 and S252, the MRI apparatus 100 may resume the suspended protocol from various different points. When the pulse sequence is suspended due to the detection of the movement, the MRI apparatus 100 may resume the protocol by initiating the pulse sequence from a start or by continuing the pulse sequence from a point at which image data is lastly obtained or a last MR image is generated. The MRI apparatus 100 may skip the suspended pulse sequence and may resume the protocol by initiating a next pulse sequence. An exemplary embodiment in which the MRI apparatus 100 resumes the protocol is described in greater detail below with reference to FIGS. 12 and 13.

As described above with reference to FIGS. 3 through 5, the MRI apparatus 100 may selectively suspend the protocol according to the value of the movement amount of the object. The MRI apparatus 100 may automatically or manually resume the suspended protocol. As described above, the MRI apparatus 100 may control the process of the protocol according to the movement of the object, so that the MRI apparatus 100 may efficiently obtain the MR image.

Figure 6:
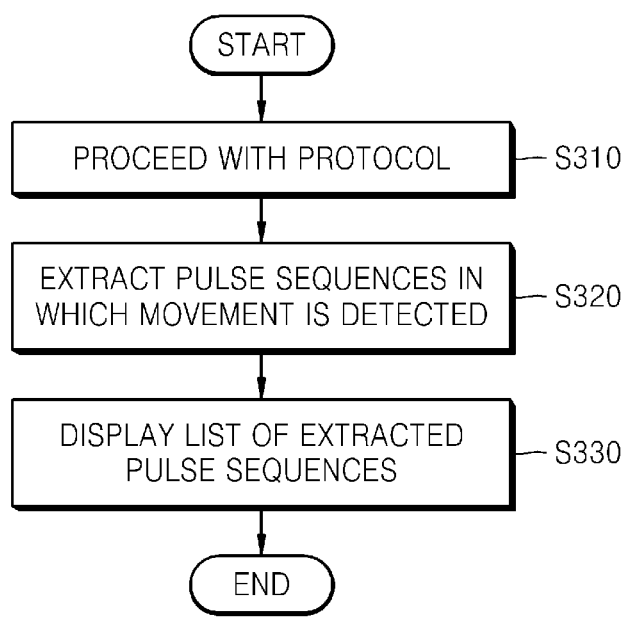
FIG. 6 is a flowchart of a method of obtaining an MR image, according to an exemplary embodiment.

FIG. 6 is a flowchart of a method of obtaining an MR image, according to an exemplary embodiment.

In operation S310, the MRI apparatus 100 proceeds with a protocol to capture an image of an object. For example, the MRI apparatus 100 may proceed with the protocol including one or more pulse sequences. In operation S320, the MRI apparatus 100 may detect movement of the object while the MRI apparatus 100 proceeds with the protocol. The feature of controlling the process of the protocol according to the detected movement of the object is the same as described above with reference to FIGS. 3 through 5.

In operation S320, the MRI apparatus 100 extracts a pulse sequence in which the movement is detected. For example, when the ongoing protocol is suspended in operation S310, the MRI apparatus 100 extracts the pulse sequence in which the movement is detected from among the pulse sequences included in the protocol. The pulse sequence in which the movement is detected may be one pulse sequence or more pulse sequences.

In operation S320, the MRI apparatus 100 may extract the pulse sequence in which a value of the detected movement is equal to or greater than a threshold value. For example, the MRI apparatus 100 may extract the pulse sequence that is suspended according to a determination result regarding comparison between the value of the detected movement and the threshold value. The MRI apparatus 100 may extract the pulse sequence based on a first marker or a second marker, which is displayed in a region on the screen which displays information about the pulse sequence.

In operation S330, the MRI apparatus 100 displays a list of extracted pulse sequences on the screen. In an exemplary embodiment, the MRI apparatus 100 may output both a list of pulse sequences included in an ended protocol and the list of the extracted pulse sequences to the screen.

In another exemplary embodiment, the MRI apparatus 100 may display a pulse sequence which has a value of the movement amount equal to or greater than a threshold value and thus is suspended, and may display another pulse sequence which has a value of movement amount less than the threshold value and thus proceeds without being suspended, as described in detail below with reference to FIG. 11.

According to the features described with reference to FIG. 6, the MRI apparatus 100 may separately output the pulse sequence of the ongoing protocol in which the movement is detected and thus may allow the user to easily recognize which pulse sequence needs to be re-executed.

Figure 7:
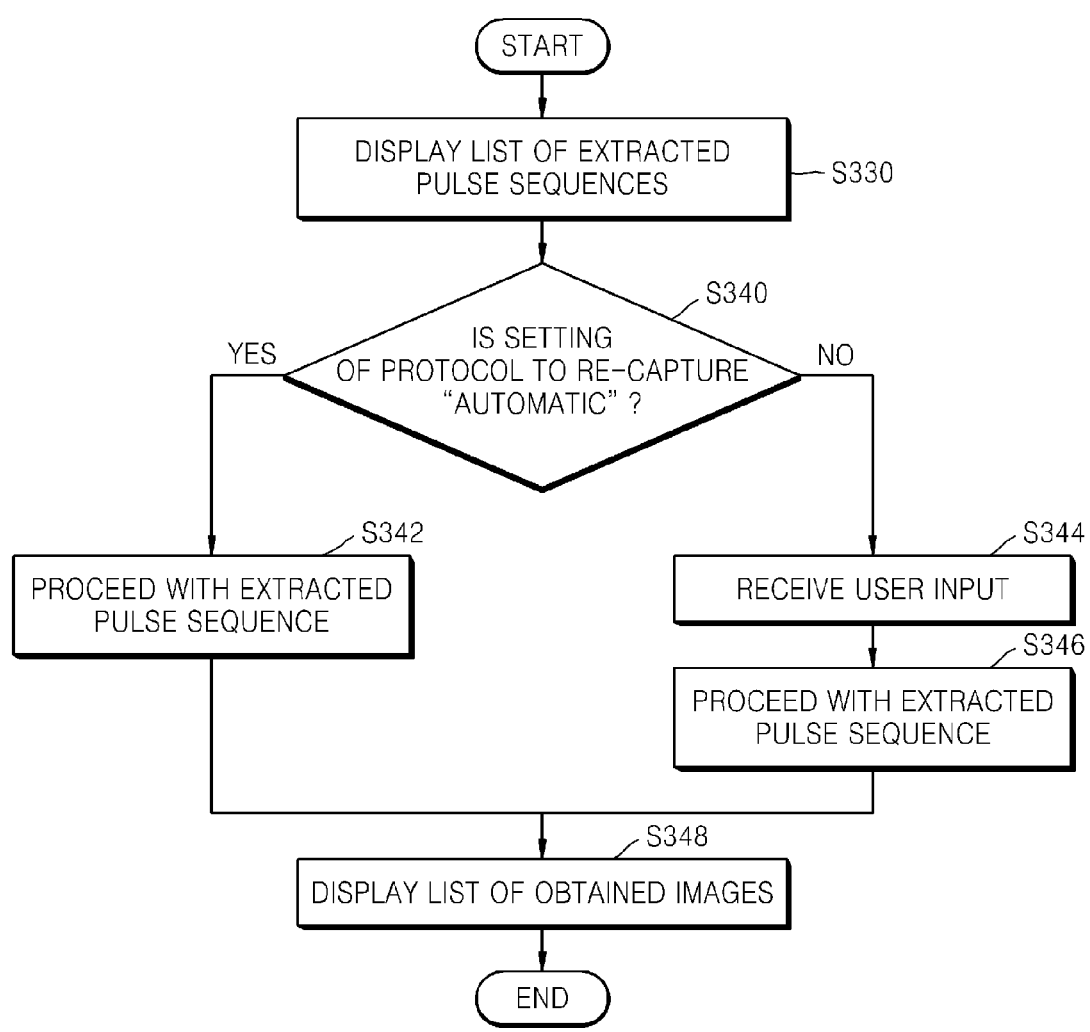
FIG. 7 is a flowchart of a method of obtaining an MR image, according to an exemplary embodiment.

FIG. 7 is a flowchart of a method of obtaining an MR image, according to an exemplary embodiment. The flowchart of FIG. 7 includes detailed operations that are performed after the list of the pulse sequences is displayed on the screen in operation S330 of the flowchart of FIG. 6.

In operation S340, the MRI apparatus 100 checks a setting value of the protocol. The setting value of the protocol, which is checked in operation S340, is different from the setting value in operation S240 of FIG. 5. For example, the MRI apparatus 100 checks whether the setting value to re-capture the extracted pulse sequences is automatic or manual. When the setting value is automatic, the MRI apparatus 100 proceeds with operation S342, and when the setting value is manual, the MRI apparatus 100 proceeds with operation S344.

In operation S342, the MRI apparatus 100 proceeds with the extracted pulse sequence. For example, the MRI apparatus 100 automatically proceeds with the extracted pulse sequence after the protocol that is suspended in operation S310 of FIG. 6, and thus re-captures an MRI mage. The MRI apparatus 100 may proceed with the list of the pulse sequences in which the movement having a value equal to or greater than the threshold value is detected, and thus may obtain the MR image in which a motion artifact does not occur.

In operation S344, the MRI apparatus 100 receives a user input of re-capturing the extracted pulse sequence, according to the list of the pulse sequences displayed on the screen. Since the setting value of the protocol is manual, the MRI apparatus 100 may stand by until a user input of proceeding with the extracted pulse sequence is received.

In an exemplary embodiment, the MRI apparatus 100 may receive a user input of selecting some pulse sequences from the list of the extracted pulse sequences displayed on the screen. For example, the MRI apparatus 100 may receive the user input of proceeding with only some pulse sequences, and not all of the extracted pulse sequences.

In operation S346, the MRI apparatus 100 proceeds with the extracted pulse sequence. For example, as described with reference to operation S342, the MRI apparatus 100 proceeds with the extracted pulse sequence and then obtains an MR image again. In an exemplary embodiment, when the MRI apparatus 100 receives an input of selecting some pulse sequences in operation S344, the MRI apparatus 100 may proceed with only the selected pulse sequences.

In operation S348, the MRI apparatus 100 displays a list of obtained MR images on the screen. For example, the MRI apparatus 100 may display the MR images, which are obtained in correspondence to the extracted pulse sequences, in operations S342 and S346. In an exemplary embodiment, the MRI apparatus 100 may display the list of the MR images that are obtained according to the extracted pulse sequences, as a separate list from a list of the MR images that is obtained after the protocol ends.

According to the features described with reference to the flowchart of FIG. 7, the MRI apparatus 100 may selectively proceed again with the pulse sequences in which the movement is detected and thus may obtain the MR images without a motion artifact. The MRI apparatus 100 may need to proceed again with an entire protocol or may proceed with only the pulse sequences in which the movement is detected, so that it is possible to save time taken to perform an image re-capturing operation, and simultaneously, it is possible to estimate a time period required to perform the image re-capturing operation.

Figure 8:
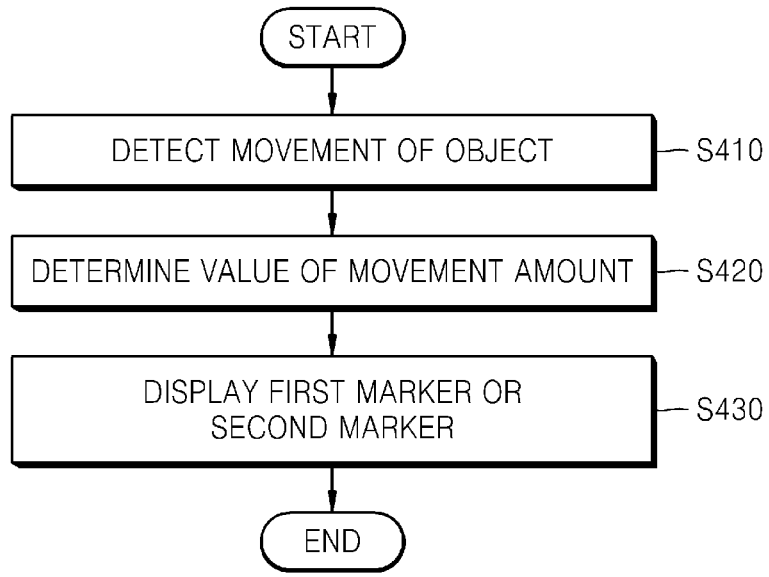
FIG. 8 is a flowchart of a method of providing information, according to an exemplary embodiment.

FIG. 8 is a flowchart of a method of providing information, performed by the MRI apparatus 100, according to an exemplary embodiment.

In operation S410, the MRI apparatus 100 detects movement of an object while a protocol proceeds. Since operation S410 shown in the flowchart of FIG. 8 is the same as operation S210 in the flowchart of FIG. 3, detailed descriptions thereof are omitted here.

In operation S420, the MRI apparatus 100 determines a value of the detected movement. For example, the MRI apparatus 100 may compare the value of the detected movement with a predetermined threshold value and then may determine whether the value is equal to or greater than the threshold value. As described above with reference to FIG. 1, the threshold value may be defined according to various references and may vary according to an ongoing protocol and pulse sequence.

In operation S430, the MRI apparatus 100 displays a first marker or a second marker on a screen. When the value of the detected movement is equal to or greater than the threshold value, the MRI apparatus 100 may display the first marker indicating that the protocol is suspended. When the value of the detected movement is less than the threshold value, the MRI apparatus 100 may display the second marker indicating that the protocol is not suspended and an MR image is compensated.

Also, in operation S430, the MRI apparatus 100 may display the first marker or the second marker on a region of the screen which displays information about the pulse sequence in which the movement is detected. For example, the MRI apparatus 100 may display in which pulse sequence the movement is detected while the protocol proceeds.

The MRI apparatus 100 may display the first marker or the second marker on a predetermined location of an obtained MR image. The MRI apparatus 100 may display a marker on an MR image of a suspended protocol or a compensated MR image. According to the method described with reference to FIG. 8, the MRI apparatus 100 displays the pulse sequence and MR image in which the movement is detected, by using the marker, so that the MRI apparatus 100 allows a user to easily distinguish the pulse sequence and MR image in which the movement is detected, from a pulse sequence and MR image in which movement is not detected. Therefore, the user of the MRI apparatus 100 may easily identify the pulse sequence and MR image in which the movement is detected and may determine whether to perform an image re-capturing operation.

Figure 9:
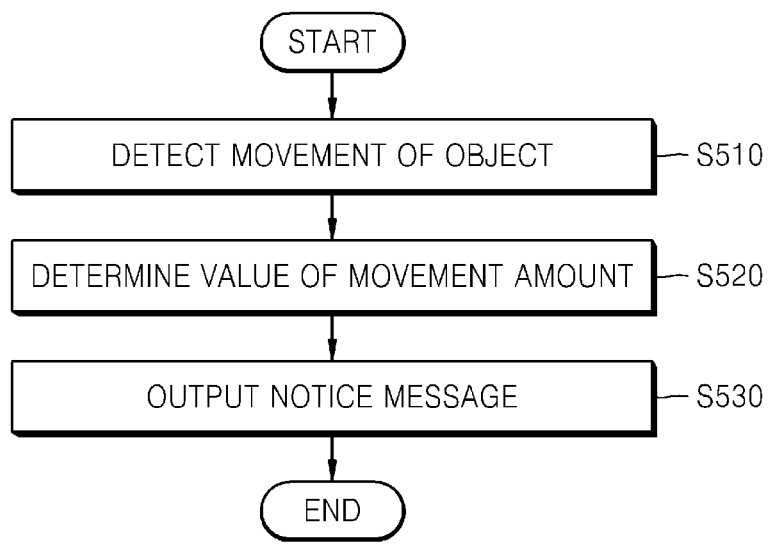
FIG. 9 is a flowchart of a method of providing information, according to an exemplary embodiment.

FIG. 9 is a flowchart of a method of providing information, performed by the MRI apparatus 100, according to an exemplary embodiment.

In operation S510, the MRI apparatus 100 detects movement of an object while a protocol proceeds. Since operation S510 shown in the flowchart of FIG. 9 is the same as operation S210 in the flowchart of FIG. 3, detailed descriptions thereof are omitted here. In an exemplary embodiment, the MRI apparatus 100 may detect movement by using one or more sensors or may detect the movement according to blurring or a noise which occurs in an obtained MR image.

In operation S520, the MRI apparatus 100 determines a value of the detected movement. In operation S520, the MRI apparatus 100 determines the value in a manner similar to operation S420 of the flowchart of FIG. 8, thus, detailed descriptions thereof are omitted here. A threshold value in operation S520 may be different from the threshold value in operation S420.

In operation S530, the MRI apparatus 100 outputs information indicating the occurrence of the movement of the object which is detected in operation S510, according to a result of the comparison between the value of the movement and the threshold value in operation S520.

For example, when the MRI apparatus 100 determines that the value of the movement by the object is equal to or greater than the threshold value, in operation S530, the MRI apparatus 100 may output the information indicating the occurrence of the movement. On the other hand, when the MRI apparatus 100 determines that the value of the movement by the object is less than the threshold value, the MRI apparatus 100 may determine that the movement is ignorable, thereby not outputting any information.

The threshold value that is a reference of whether to output the information indicating the occurrence of the movement may be different from the threshold value described above with reference to FIGS. 3 through 8. For example, according to the description above, the threshold value means the level of the detected movement at which the MRI apparatus 100 determines whether to resume or to continue the protocol. The threshold value may vary according to a user input or an internal algorithm of a system as described above with reference to FIGS. 1 and 2. In an exemplary embodiment, the threshold value may be a reference value by which the MRI apparatus 100 determines whether the detected movement is ignorable, i.e., the threshold value may be the reference value by which the MRI apparatus 100 determines whether a re-capturing operation is needed.

In more detail, when the MRI apparatus 100 determines that the level of the movement is equal to or greater than the threshold value in operation S520, the MRI apparatus 100 may output the information, in operation S530, indicating the occurrence of the movement to a user, without suspending the protocol.

The MRI apparatus 100 may display a first marker indicating the occurrence of the movement with respect to the pulse sequence in which the movement equal to or greater than the threshold value is detected. However, in the present exemplary embodiment, a marker that is displayed on a region in which the pulse sequence is displayed or on the MR image may be different from the first marker described above. For example, the first marker described above with reference to FIGS. 3 through 9 corresponds to a marker at which the movement is detected and thus the protocol is suspended. However, the first marker in the present embodiment may correspond to a marker at which the movement equal to or greater than the threshold value is detected. For example, the term "first marker" or "second marker" is used to distinguish an order of markers or meanings of the markers, thus, the exemplary embodiments are not limited to the term.

When the MRI apparatus 100 determines that the level of the movement is less than the threshold value, the MRI apparatus 100 does not output any information to a user and may compensate the MR image as shown in operations S236 and S238 of the flowchart of FIG. 4. As described above, in a case where the MRI apparatus 100 compensates for the MR image, the second marker may be displayed.

In an exemplary embodiment, the MRI apparatus 100 may output movement occurrence information indicating the occurrence of the movement in operation S530, and may extract and proceed with the pulse sequence in which the movement is detected, as described with reference to FIGS. 6 and 7. The MRI apparatus 100 may automatically proceed with the extracted pulse sequence after the protocol is ended or may proceed with the extracted pulse sequence in response to a user input.

The MRI apparatus 100 may output a notice message indicating the movement occurrence information by using at least one of graphical data, text data, and audio data. For example, the MRI apparatus 100 may output the notice message by using the text data or the graphical data which is displayed on a pop-up window indicating the detection of the movement, or may output the notice message by using an alarm sound or pre-stored audio data.

FIG. 10 illustrates examples of detecting movement of an object while a protocol proceeds, according to exemplary embodiments. As described above with reference to FIGS. 1 and 2, the MRI apparatus 100 may detect the movement of the object by using various types of sensors, by using an image-capturing device, or by comparing MR images.

In FIG. 10A, the MRI apparatus 100 proceeds with a protocol of capturing an image of an object 830 positioned on a cradle 820 that moves into a bore 810. An image-capturing device 840 in a shield room 800 obtains image data by capturing an image of the object 830 while the protocol proceeds. Afterward, the sensor 120 of the MRI apparatus 100 may analyze the image data and thus may detect whether the object 830 moves during an image-capturing operation.

The sensor 120 of the MRI apparatus 100 may detect the movement of the object 830 by analyzing the image data obtained from the image-capturing device 840 and the MRI apparatus 100 may display the image data to a user to allow the user to check the movement of the object 830.

In FIG. 10B, similarly to the example of FIG. 10A, an image-capturing device 850 disposed in a bore 810 detects movement of an object 830 while a protocol proceeds. The image-capturing devices 840 and 850 of FIGS. 10A and 10B may be replaced by an optical sensor such as an infrared-ray sensor, or the sensors described above with reference to FIG. 1 may be used.

In FIG. 10C, an image-capturing device 860 may be attached to an object 830. In the example of FIG. 10C, the image-capturing device 860 does not observe the object 830 but observes an inside of a bore 810. In a case where a marker to identify an inner image of the bore 810 exists, the MRI apparatus 100 may analyze the inner image of the bore 810 which is obtained by the image-capturing device 860 and may detect whether the object 830 moves. For example, the image-capturing device 860 attached to the object 830 may move according to the movement of the object 830, and the movement of the image-capturing device 860 may cause shaking or variation in the inner image of the bore 810. In addition to the example shown in FIG. 10C, the image-capturing device 860 may be attached to an RF coil and may capture the inner image of the bore 810.

FIG. 11 illustrates a method of displaying a marker indicating movement of an object which is detected while a protocol proceeds, according to an exemplary embodiment.

FIG. 11A illustrates information about a protocol and pulse sequences which is displayed on a screen of the MRI apparatus 100. In FIG. 11A, the MRI apparatus 100 displays eight pulse sequences, which are included in a brain protocol, on the screen. The eight pulse sequences shown in FIG. 11A are displayed on the screen by using respective parameters indicating a particular area of an object, an image-capturing direction, and an image-capturing method. For example, the MRI apparatus 100 may display "Preview Scan" and "t2_haste_tra_8 mm free br" that are parameters for defining the first and second pulse sequences, respectively.

In FIG. 11A, the MRI apparatus 100 displays a marker 910 on the screen, which indicates that movement is detected while the second pulse sequence proceeds. For example, the marker 910 that is displayed on a left side of the parameter of the second pulse sequence may indicate that the pulse sequence is suspended due to detection of an object movement during an execution of the pulse sequence. In another exemplary embodiment, the marker 910 may indicate the suspension of the protocol and the pulse sequence or may indicate the detection of the movement that is equal to or greater than a threshold value.

In FIG. 11A, the MRI apparatus 100 shows a situation in which, after the first and second pulse sequences are ended, movement is detected during an execution of a third pulse sequence so that the protocol is suspended. Unlike the first and second pulse sequences, an area of the third pulse sequence is divided into a dark area 912 and a bright area 915. As the third pulse sequence proceeds, the MRI apparatus 100 may increase the dark area in a direction from a left side of FIG. 11A toward a right side. In FIG. 11A, the movement of an object is detected when the process of the third pulse sequence is complete about 80%. The fourth through eighth pulse sequences in bright areas indicate that they have not started yet.

When the MRI apparatus 100 detects the movement of the object, the MRI apparatus 100 may output information about the detected movement. In FIG. 11B, the MRI apparatus 100 outputs the information about the movement to the screen by using an image and a text. As shown in FIG. 11B, when a setting value with respect to protocol suspension is automatic, the MRI apparatus 100 outputs a message "movement is detected" to the screen, to inform that the movement having a value equal to or greater than a threshold value is detected. When an input of resuming the third pulse sequence is received from a user, the MRI apparatus 100 may resume the suspended protocol. Alternatively, the MRI apparatus 100 may receive an input of starting the third pulse sequence again from the beginning or an input of skipping the suspended protocol and starting a next pulse sequence.

In FIG. 11C, the MRI apparatus 100 outputs the information about the detected movement by using audio data. For example, the MRI apparatus 100 may output a notice message, such as an alarm sound, to the user by using an audio signal.

Also, as described above, the MRI apparatus 100 may suspend a next pulse sequence which follows the pulse sequence in which the movement is detected. For example, when movement having a value equal to or greater than a threshold value is detected while the third pulse sequence shown in FIG. 11A proceeds, the MRI apparatus 100 may continue the third pulse sequence and then may stand by instead of starting a fourth pulse sequence.

FIG. 12 illustrates an example of resuming a suspended pulse sequence, according to an exemplary embodiment. Pulse sequences 909, 911, 913, and 916 are schematically illustrated in FIGS. 12A through 12D, respectively. An arrow 900 shown in FIG. 12A means that the pulse sequences proceed in a direction from a left side to a right side.

Figure 12A:
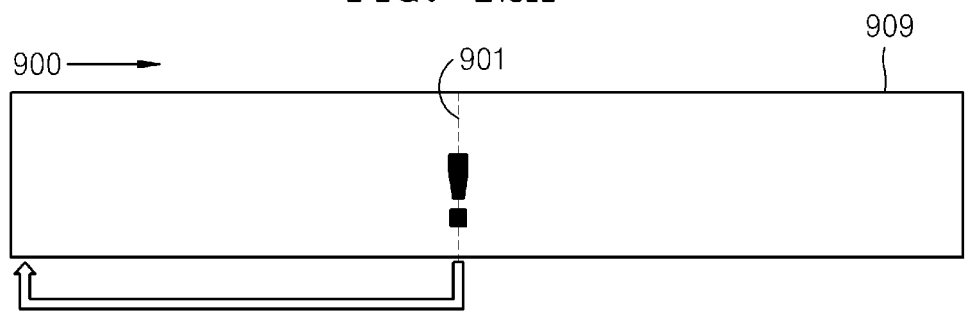
FIGS. 12A, 12B, 12C, and 12D illustrate an example of resuming a suspended pulse sequence, according to an exemplary embodiment.

In FIG. 12A, while a protocol proceeds, the MRI apparatus 100 detects movement of an object at a position 901 and suspends the protocol. When the MRI apparatus 100 does not detect the movement any more or the suspended protocol is resumed in response to a user input, the MRI apparatus 100 may capture an image of the suspended protocol from a start of the pulse sequence 909.

For example, in FIG. 12A, image data of the object is obtained when the pulse sequence is ended. Accordingly, when the MRI apparatus 100 detects the movement while the protocol proceeds, the MRI apparatus 100 re-starts the pulse sequence from a start.

Figure 12B:
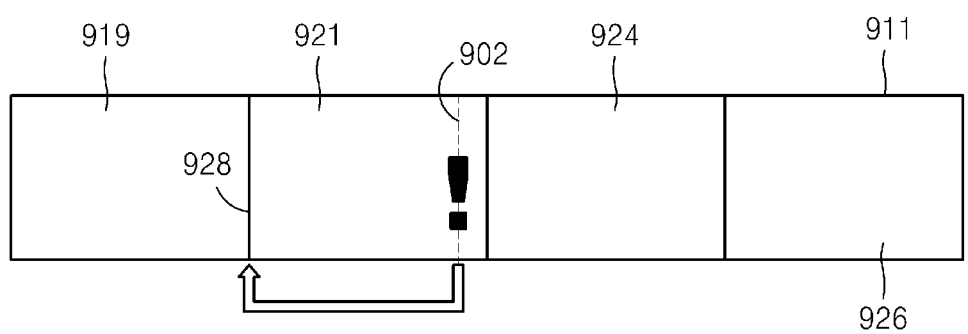

In FIG. 12B, while a pulse sequence 911 proceeds, the MRI apparatus 100 detects movement of an object at a position 902 and suspends a protocol (i.e., the pulse sequence). The MRI apparatus 100 does not resume the suspended pulse sequence from a start of the pulse sequence 911.

FIG. 12B illustrates the pulse sequence 911 formed of four areas 919, 921, 924, and 926. The image data of the object is obtained four times from four areas, respectively, when the pulse sequence 911 proceeds. When the MRI apparatus 100 detects the movement of the object at the position 902, the MRI apparatus 100 may resume the suspended pulse sequence from a point at which obtainment of MR image data is completed. For example, the MRI apparatus 100 may resume the pulse sequence from a point 928 between the area 919 and the area 921, at which image data is lastly obtained before the pulse sequence is suspended.

Figure 12C:
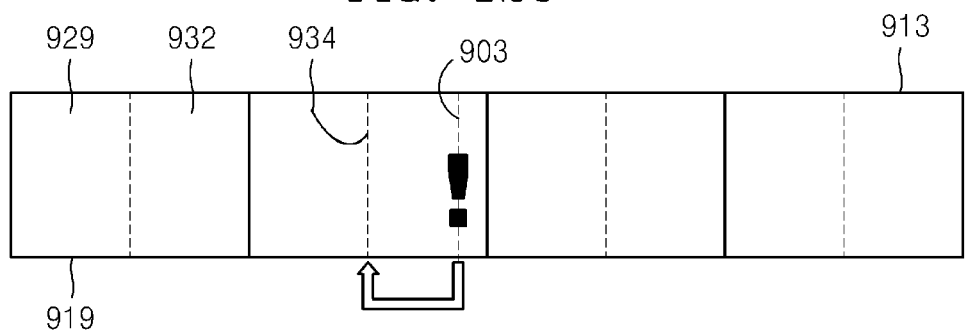

In FIG. 12C, the MRI apparatus 100 obtains image data four times in four areas 919, 921, 924, and 926, but generates two MR images from two sub-areas 929 and 932, for example, of the area 919, while the image data is obtained only once in each of the areas 919, 921, 924, and 926. For example, the MRI apparatus 100 generates a total of eight MR images via the pulse sequence 913 of FIG. 12C.

When movement of the object is detected at a position 903, the MRI apparatus 100 may resume the suspended pulse sequence from a point 934 between two sub-areas, at which an MR image is lastly generated.

Figure 12D:
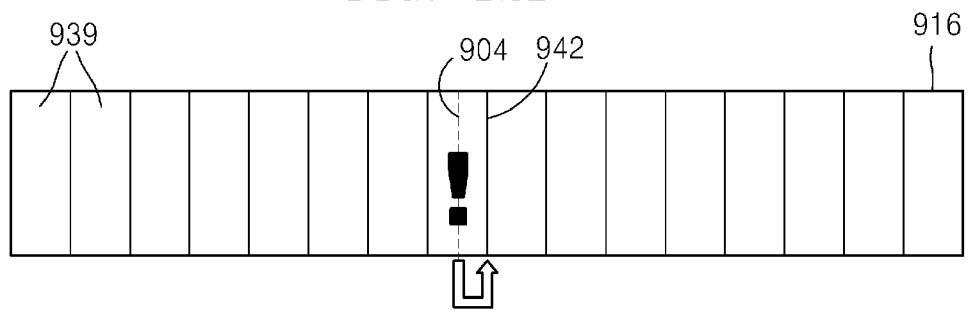

In FIG. 12D, the MRI apparatus 100 sequentially generates a plurality of MR images in the adjacent areas 939 via a pulse sequence 916. When the MRI apparatus 100 detects movement of an object at a position 904, the MRI apparatus 100 may skip an MR image in which the movement is detected, and may resume the pulse sequence at the start point 942 of the next adjacent area to generate a next MR image.

For example, in FIG. 12D, when the MRI apparatus 100 detects movement at the position 904 of the pulse sequence, the MRI apparatus 100 may resume the pulse sequence in succession to the position 904. Accordingly, an MR image corresponding to the position 904 may include a motion artifact or may be incomplete but the MRI apparatus 100 may obtain another complete MR image from the plurality of MR images.

According to the exemplary embodiments of FIGS. 12A through 12D, the MRI apparatus 100 may vary a method and a position that involve resuming the protocol, according to types of the pulse sequence and the protocol. The MRI apparatus 100 may determine in advance whether a method of obtaining image data and generating an MR image is a serial-type method or a parallel-type method, and may resume the suspended protocol and/or pulse sequence based the determination. For example, in FIG. 12A, when image data is obtained once by capturing an image of the object in a parallel manner, the MRI apparatus 100 may re-capture the image of the suspended pulse sequence from a start.

In addition to the exemplary embodiments described with reference to FIGS. 12A through 12D, the MRI apparatus 100 may suspend and resume the pulse sequence by using various methods. For example, a procedure in which the MRI apparatus 100 proceeds with the pulse sequence is not limited to the described above.

FIG. 13 illustrates an example of resuming a suspended pulse sequence, according to an exemplary embodiment. A block 905 shown in FIGS. 13A and 13B indicates a protocol, and a plurality of bars 906 that form the block 905 respectively indicate first through seventh pulse sequences included in the protocol.

In FIG. 13A, the MRI apparatus 100 detects movement of an object at a position 907 while a third pulse sequence 950 proceeds. The MRI apparatus 100 may capture again an image of the third pulse sequence by using the various methods described above with reference to FIGS. 12A through 12D.

In FIG. 13B, the MRI apparatus 100 detects movement of the object at a position 908 of the third pulse sequence. Unlike FIG. 13A, the MRI apparatus 100 may skip the third pulse sequence in which the movement is detected and may start a fourth pulse sequence 952. The MRI apparatus 100 may proceed with the third pulse sequence in which the movement is detected, after the protocol is ended, as schematically illustrated by an area 954 at the bottom of a block 905. As described with reference to FIG. 7, the MRI apparatus 100 may automatically proceed with the third pulse sequence or may proceed with the third pulse sequence in response to a user input. Embodiments related to FIG. 13B are described in detail with reference to FIGS. 14 and 15.

FIG. 14 illustrates an example of outputting a list of suspended pulse sequences from among one or more pulse sequences included in a protocol, according to an exemplary embodiment.

In FIG. 14A, the MRI apparatus 100 dims areas of a screen on which eight pulse sequences included in a brain protocol are displayed and thus shows that eight pulse sequences have proceeded. Three markers 910 that are displayed with respect to the second, fourth, and sixth pulse sequences by the MRI apparatus 100 indicate that the second, fourth, and sixth pulse sequences are suspended since movement having a value equal to or greater than a threshold value is detected.

In FIG. 14B, the MRI apparatus 100 extracts pulse sequences in which movement having a value equal to or greater than a threshold value is detected, and displays the extracted pulse sequences on the screen. For example, the MRI apparatus 100 may extract the second, fourth, and sixth pulse sequences from eight pulse sequences included in the brain protocol and may display a list of the extracted second, fourth, and sixth pulse sequences on the screen.

In FIG. 14B, the MRI apparatus 100 may extract pulse sequences based on values of movements that are detected in the pulse sequences, respectively, or may extract pulse sequences having the markers 910.

Although not illustrated in FIG. 14, the MRI apparatus 100 may output the list of the extracted second, fourth, and sixth pulse sequences on the screen as shown in FIG. 14B and then may automatically or manually proceed with the extracted second, fourth, and sixth pulse sequences. For example, when a setting value with respect to the extracted pulse sequences is automatic, the MRI apparatus 100 may output the extracted pulse sequences to the screen, proceed again with the extracted pulse sequences, and newly obtain an MR image. On the other hand, when the setting value with respect to the extracted pulse sequences is manual, the MRI apparatus 100 may output the extracted pulse sequences to the screen and then may receive a user input of processing the extracted pulse sequences while the MRI apparatus 100 stands by. For example, the MRI apparatus 100 may proceed with the extracted pulse sequences, may disregard the extracted pulse sequences, and then may end the protocol, or may receive a user input of selecting and proceeding with some extracted pulse sequences and then may operate according to the received user input.

FIG. 15 illustrates an example of separately outputting a list of suspended pulse sequences and a list of pulse sequences in which MR images are automatically compensated, according to an exemplary embodiment.

In FIG. 15A, the MRI apparatus 100 outputs a feature to a screen to indicate that movement having a value less than a threshold value is detected while a seventh pulse sequence proceeds. For example, markers 914 with a black frame which are displayed in second, fourth, and sixth pulse sequences are first markers indicating that movement having a value equal to or greater than the threshold value is detected during execution of the second, fourth, and sixth pulse sequences so that the second, fourth, and sixth pulse sequences are suspended. A marker 920 with a white frame which is displayed in the seventh pulse sequence may be a second marker indicating that the movement having the value less than the threshold value is detected so that the seventh pulse sequence is not suspended and an MR image is automatically compensated.

In FIG. 15A, the first markers and the second marker are distinguished from each other by using colors but they may be distinguished from each other by using various other methods. For example, the MRI apparatus 100 may distinguish between two types of markers by using various visual effects, such as colors, shapes, sizes, transparency, or the like, of the markers. In addition, the markers shown in FIGS. 9 through 15 may be exemplary to display the detected movement, and the MRI apparatus 100 may output the markers to the screen by using various shapes and manners. For example, the MRI apparatus 100 may display a marker having a random shape or may distinguish between a color of an area of a pulse sequence in which movement is detected and a color of another area. For example, the MRI apparatus 100 may visually emphasize the pulse sequence in which movement is detected, by using various methods without displaying an additional marker, and may output the pulse sequence.

In FIG. 15B, the MRI apparatus 100 extracts a list of pulse sequences in which movement is detected and displays the list on the screen. Unlike the exemplary embodiment of FIG. 14B, in FIG. 15B, the MRI apparatus 100 may extract second, fourth, and sixth pulse sequences of which a value of the movement is equal to or greater than the threshold value and also may extract the seventh pulse sequence of which a value of the movement is less than the threshold value and may display the seventh pulse sequence on the screen 922.

For example, the MRI apparatus 100 may distinguish between pulse sequences of which a value of movement is equal to or greater than a threshold value and pulse sequences of which a value of movement is less than the threshold value and may output them to the separate areas of screen. Accordingly, when a setting value with respect to extracted pulse sequences is automatic, the MRI apparatus 100 may output both types of the pulse sequences to the screen, and then may proceed with only pulse sequences that have been suspended or may proceed with all of the pulse sequences that have been suspended and pulse sequences of which MR images are compensated. For example, the MRI apparatus 100 may proceed again with all of the pulse sequences in which movement is detected.

Figure 16:
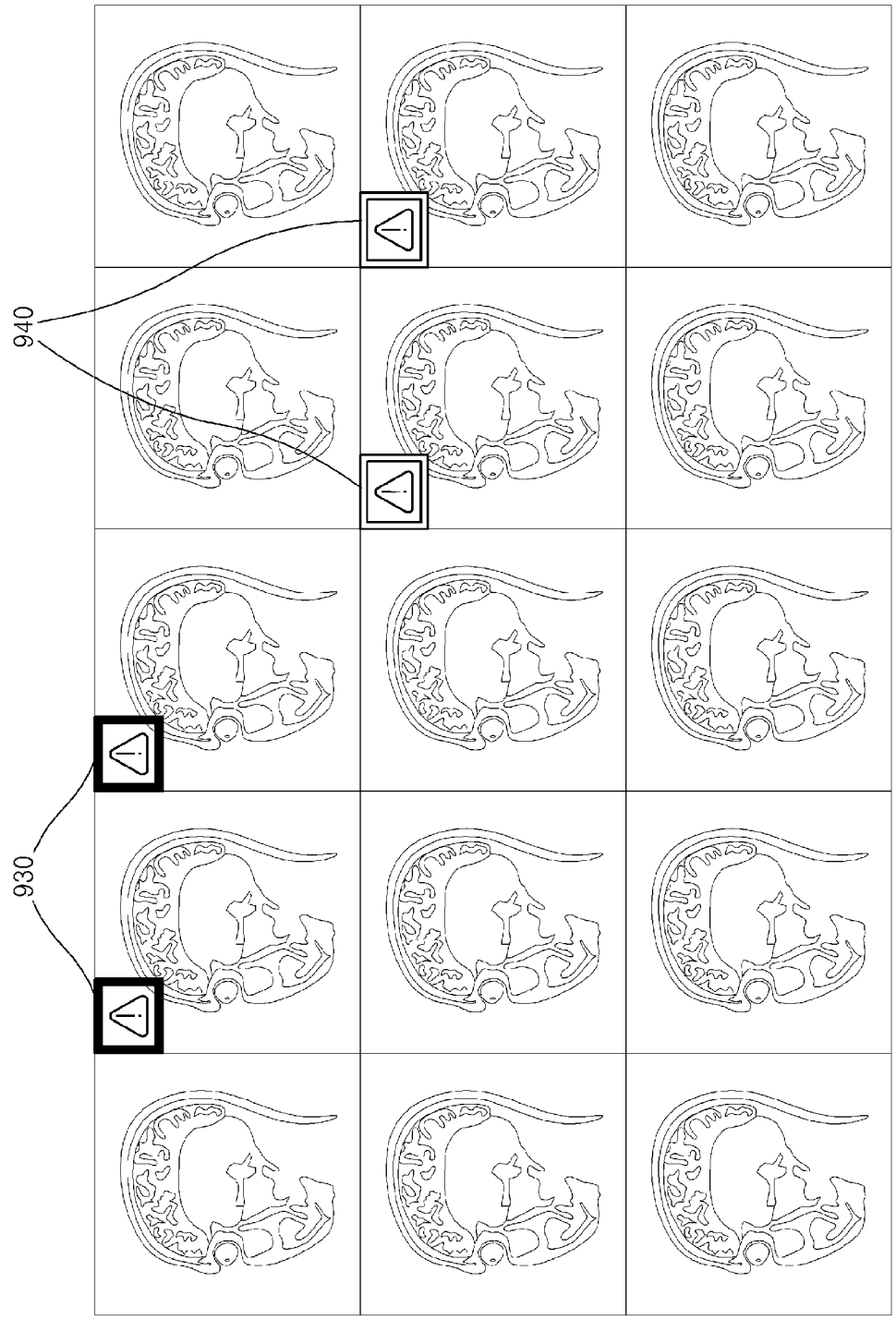
FIG. 16 illustrates an example in which a marker is displayed on some MR images, which are obtained via pulse sequences in which movement of an object is detected, according to an exemplary embodiment.

FIG. 16 illustrates an example in which a marker is displayed on some MR images from among a plurality of MR images, which are obtained via pulse sequences in which movement of an object is detected, according to an exemplary embodiment.

Fifteen images shown in FIG. 16 are MR images obtained by capturing an image of a head of an object from a sagittal view. The MRI apparatus 100 may capture approximately 10 through 20 MR images with respect to one pulse sequence, although there is a difference in each of the pulse sequences.

Markers 930 with a black frame shown in FIG. 16 indicate MR images in which movement equal to or greater than a threshold value is detected while a pulse sequence proceeds, or in which an image-capturing operation is suspended and then is resumed due to the movement, and markers 940 with a white frame indicate MR images that are automatically compensated since movement less than the threshold value is detected.

For example, the MRI apparatus 100 may display the MR images, in which the movement of the object is detected during a process of a protocol, by using a marker on a list of the MR images displayed on a screen. The MRI apparatus 100 may separately display the MR images based on how the MR images are processed according to the value of the detected movement, by using various types of markers.

Therefore, a user of the MRI apparatus 100 may easily observe which MR image needs to be re-captured, or whether the MR images that are compensated by using a motion correction algorithm are sufficient to be read.

In another exemplary embodiment, the MRI apparatus 100 may extract only a list of some MR images in which movement is detected from among a plurality of obtained MR images and may display the list of some MR images. For example, similarly to the extraction of the pulse sequences in FIG. 15, the MRI apparatus 100 may extract MR images in which movement equal to or greater than a threshold value is detected, and/or compensated MR images from among the plurality of obtained MR images, and may display them on the screen. Accordingly, the user of the MRI apparatus 100 may easily detect the MR images in which movement is detected.

The markers shown in FIG. 16 are exemplary only and thus various different types of markers and displaying methods may be used. For example, the MRI apparatus 100 may flicker an MR image in which movement is detected from among the plurality of obtained MR images displayed on the screen or may apply a visual effect to a frame of an MR image (e.g., the MRI apparatus 100 may emphasize the frame of the MR image or may change a color of the frame).

FIG. 17 illustrates examples of a marker displayed on a screen, according to an exemplary embodiment. FIG. 17 illustrates the example of a graphical user interface (GUI) with respect to the marker described above with reference to FIG. 16, by illustrating MR images. While the exemplary embodiment of FIG. 17 is related to the GUI with respect to the MR image, the exemplary embodiment of FIG. 17 may be equally applied to a region of displaying information that corresponds to a pulse sequence as illustrated in FIGS. 14 and 15.

As shown in FIG. 17A, the MRI apparatus 100 may display a marker having a predetermined shape on a partial region of an image 1050. As shown in FIG. 17B, the MRI apparatus 100 may change a color or a gray scale of an image 1060, thereby differentiating the image 1060 from another MR image in which movement is not detected. Alternatively, the MRI apparatus 100 may blink an image 1060, thereby indicating detection of movement.

As shown in FIG. 17C, the MRI apparatus 100 may apply a visual effect to an outline of an MR image 1070 or may display a text message on an MR image 1080 as shown in FIG. 17D.

The examples of FIG. 17 are shown to describe the exemplary embodiment of displaying a marker, by the MRI apparatus 100. However, one or more exemplary embodiments are not limited to the exemplary embodiment of FIG. 17.

FIG. 18 illustrates an example of outputting information indicating detection of movement according to the movement of an object, according to an exemplary embodiment. When the MRI apparatus 100 detects the movement of the object while a protocol and pulse sequences proceed, the MRI apparatus 100 may output information on a screen 1000. FIG. 18 illustrates the example in which the MRI apparatus 100 displays a notice message by using a pop-up window 1005.

In FIG. 18, a level of the detected movement is equal to or greater than the threshold value described with reference to FIG. 9. For example, when the MRI apparatus 100 determines that the movement of the object is equal to or greater than the threshold value, by comparing image characteristic values of the one or more sensors or MR images, the MRI apparatus 100 may output movement occurrence information, regardless of the process of the protocol.

Afterward, when the protocol is ended, and a user checks an MR image and selects a re-capturing operation, the MRI apparatus 100 may re-capture an image of a pulse sequence in which the movement is detected or may automatically perform the re-capturing operation.

The example of FIG. 18 shows the notice message for indicating the movement occurrence information, so that the MRI apparatus 100 may provide the user with the information indicating the occurrence of the movement by outputting various notice messages such as "re-capturing operation due to detection of movement", "Please check an image with a marker and select whether to perform a re-capturing operation", or the like. A method of providing information, by the MRI apparatus 100, is not limited to the shown graphic or text message, and thus, as described above, the MRI apparatus 100 may use previously-stored audio data.

FIG. 19 illustrates an example of outputting a notice message about a process of a protocol, in response to movement of an object, according to an exemplary embodiment. The MRI apparatus 100 outputs the notice message by displaying a pop-up window 1010 on a screen 1000. As described above with reference to FIG. 9, the MRI apparatus 100 may output an alarm sound or audio data together with the pop-up window 1010.

In FIG. 19, a value of the movement of the object is less than a threshold value. The MRI apparatus 100 does not suspend the protocol, and controls the process of the protocol to compensate an obtained MR image.

The MRI apparatus 100 may display a marker on a region that displays a pulse sequence or on an MR image and may also display information about detected movement. For example, the MRI apparatus 100 may output a notice message indicating information about the process of the protocol, by using at least one of graphical data, text data, and audio data.

The pop-up window 1010 shown in FIG. 19 is an example of the output notice message, and the MRI apparatus 100 may output the notice message by using at least one of graphical data, text data, and audio data in different forms. If the detected movement is equal to or greater than the threshold value, the MRI apparatus 100 may output a notice message saying "Detected movement cannot be compensated. The protocol is suspended." Alternatively, the MRI apparatus 100 may output a notice message saying "Detected movement cannot be compensated. An image re-capturing operation will be performed.", and may control the process of the protocol according to the notice message.

In an exemplary embodiment, the MRI apparatus 100 may output a notice message and may proceed with a suspended protocol in response to a confirmation input that is received by touching or clicking a confirmation button 1020 by a user. When the protocol is not suspended, the MRI apparatus 100 may end an output of the notice message in response to the confirmation input.

According to one or more exemplary embodiments, the MRI apparatus 100 controls a process of a protocol and/or of one or more pulse sequences in response to detection of movement of an object while an MR image is captured, so that the MRI apparatus 100 may minimize occurrence of a motion artifact in the obtained MR image. The MRI apparatus 100 may notify a user that the movement of the object is detected, and thus may allow the user to immediately recognize a situation in which the movement of the object is detected.

In addition, the MRI apparatus 100 displays a marker on the pulse sequences and an image in which the movement of the object is detected, so that the user of the MRI apparatus 100 may easily recognize the pulse sequences and the image which needed to be checked for motion artifacts. The MRI apparatus 100 extracts and proceeds with only the pulse sequences in which the movement of the object is detected, so that the user of the MRI apparatus 100 may easily configure a list of the pulse sequences in which a motion artifact occurs and may easily estimate a time period required to perform an image re-capturing operation, so that the user may efficiently image and diagnose the object.

Exemplary embodiments can be implemented as computer programs and in general-use computers that execute the programs using a computer-readable recording medium. Data structures used in exemplary embodiments can be written in a computer-readable recording medium through various means. Examples of the computer-readable recording medium include magnetic storage media (e.g., ROM, floppy disks, hard disks, etc.), optical recording media (e.g., CD-ROMs, or DVDs), etc.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A magnetic resonance imaging (MRI) method comprising:
   obtaining information for movement of an object while a protocol comprising a plurality of pulse sequences is executed to capture an image of a region of the object; and
   outputting information indicating occurrence of the movement of the object on a screen, based on the information for movement,
   wherein the information indicating the occurrence of the movement of the object identifies a title of at least one pulse sequence in which the object movement is detected, of the plurality of pulse sequences, and
   the outputting comprises:
   displaying a first marker on an area of the screen in which the title of the pulse sequence in which the movement is detected is displayed, when a value of a movement amount is equal to or greater than a threshold value, and
   displaying a second marker on the area of the screen in which the title of the pulse sequence in which the movement is detected is displayed, when the value of the movement amount is less than the threshold value,
   wherein the first marker and the second marker are displayed differently from each other, and
   the method further comprises:
   extracting the at least one pulse sequence included in the protocol in which the movement is detected; and
   displaying a title of the at least one extracted pulse sequence in a list on the screen.

2. The method of claim 1, wherein the outputting the information indicates the occurrence of the movement of the object comprises additionally outputting a notice message indicating the occurrence of the movement, by using at least one among graphical data, text data, and audio data.

3. The method of claim 1, wherein the extracting the at least one pulse sequence comprises:
   extracting the at least one pulse sequence included in the protocol in which the movement is detected when an execution of the protocol is ended.

4. The method of claim 3, wherein the extracting comprises extracting the at least one pulse sequence in which the value of the movement amount of the object is equal to or greater than the threshold value.

5. The method of claim 3, wherein the extracting comprises extracting the at least one pulse sequence in which the first graphical marker is displayed.

6. The method of claim 3, wherein the displaying comprises displaying a pulse sequence in which the value of the movement amount of the object is equal to or greater than the threshold value to be visually different from a display of a pulse sequence in which the value of the movement amount of the object is less than the threshold value.

7. The method of claim 3, further comprising re-executing the at least one extracted pulse sequence after the protocol is ended.

8. The method of claim 3, further comprising re-executing the at least one extracted pulse sequence based on a user input.

9. A magnetic resonance imaging (MRI) apparatus comprising:
   a memory configured to store at least one instruction;
   at least one processor configured to, by executing the at least one instruction stored in the memory, execute a protocol comprising a plurality of pulse sequences to capture an image of a region of an object,
   obtain information for movement of the object while the protocol is executed, and generate information indicating occurrence of the movement of the object based on the information for the movement; and
   an output device which outputs the information indicating the occurrence of the movement of the object on a screen,
   wherein the information indicates the occurrence of the movement of the object identifies a title of at least one pulse sequence in which the object movement is detected, of the plurality of pulse sequences,
   the output device is configured to display a first marker on an area of the screen in which the title of the pulse sequence in which the movement is detected is displayed, when a value of a movement amount is equal to or greater than a threshold value, and to display a second marker on the area of the screen in which the title of the pulse sequence in which the movement is detected is displayed, when the value of the movement amount is less than the threshold value,
   the first marker and the second marker are displayed differently from each other,
   the at least one processor is configured to, by executing the at least one instruction stored in the memory, extract the at least one pulse sequence included in the protocol in which the movement is detected, and
   the output device is configured to display a title of the at least one extracted pulse sequence in a list on the screen.

10. The MRI apparatus of claim 9, wherein the output device additionally outputs a notice message indicating the occurrence of the movement, by using at least one among graphical data, text data, and audio data.

11. The MRI apparatus of claim 9, wherein the at least one processor is configured to, by executing the at least one instruction stored in the memory, extract the at least one pulse sequence included in the protocol in which the movement is detected, when the protocol is ended.

12. The MRI apparatus of claim 11, wherein the at least one processor is configured to, by executing the at least one instruction stored in the memory, extract the at least one pulse sequence in which the value of the movement amount of the object is equal to or greater than the threshold value.

13. The MRI apparatus of claim 11, wherein the at least one processor is configured to, by executing the at least one instruction stored in the memory, extract the at least one pulse sequence in which the first graphical marker is displayed.

14. The MRI apparatus of claim 11, wherein the output device displays a pulse sequence in which the value of the movement amount of the object is equal to or greater than the threshold value visually different from a display of a pulse sequence in which the value of the movement amount of the object is less than the threshold value.

15. The MRI apparatus of claim 11, wherein the at least one processor is configured to, by executing the at least one instruction stored in the memory, re-execute the at least one extracted pulse sequence after the protocol is ended.

16. The MRI apparatus of claim 11, further comprising an input device which receives a user input,
wherein the at least one processor is configured to, by executing the at least one instruction stored in the memory, re-execute the at least one extracted pulse sequence based on the user input.

17. A magnetic resonance imaging (MRI) apparatus comprising:
a memory configured to store at least one instruction;
at least one processor configured to, by executing the at least one instruction stored in the memory, execute a protocol comprising a plurality of pulse sequences to capture an image of a region of an object,
obtain information for movement of the object while the protocol is executed, and generate information indicating occurrence of the movement of the object based on the information for movement; and
an output device configured to display the information indicating the occurrence of the movement of the object on a screen,
wherein reconstructed MR images, which are obtained via the plurality of pulse sequences, are displayed at a same time,
the information indicating the occurrence of the movement of the object visually identifies a reconstructed MR image, of the reconstructed MR images, which is obtained via a pulse sequence in which the movement is detected, by displaying a graphical marker on the reconstructed MR image which is obtained via the pulse sequence in which the movement is detected,
the at least one processor is configured to, by executing the at least one instruction stored in the memory, extract the reconstructed MR image, which is obtained via the pulse sequence in which the movement is detected, and
the output device is configured to display the extracted reconstructed MR image on the screen.

18. The MRI apparatus of claim 17, wherein the output device outputs a notice message indicating the occurrence of the movement, by using at least one among graphical data, text data, and audio data.

19. The MRI apparatus of claim 17, wherein the output device displays the graphical marker when a value of a movement amount of the object is equal to or greater than a threshold value.

20. The MRI apparatus of claim 19,
wherein the at least one processor is configured to, by executing the at least one instruction stored in the memory, compensate another MR image, of the reconstructed MR images, that is obtained via the pulse sequence in which the movement is detected from the plurality of pulse sequences of the protocol, when a level of the movement is less than the threshold value.

21. The MRI apparatus of claim 20, wherein the output device displays a marker indicating that the another MR image is compensated.

22. The MRI apparatus of claim 17, wherein the at least one processor is configured, by executing the at least one instruction stored in the memory, to re-execute the pulse sequence in which the movement is detected, after the protocol is ended.

23. A magnetic resonance imaging (MRI) method comprising:
obtaining information for movement of an object while a protocol comprising a plurality of pulse sequences is executed to capture an image of a region of the object;
displaying, at a same time, reconstructed MR images which are obtained via the plurality of pulse sequences; and
displaying information indicating occurrence of the movement of the object on a screen, based on the information for movement,
wherein the information indicating the occurrence of the movement of the object visually identifies a reconstructed MR image, of the reconstructed MR images, which is obtained via a pulse sequence in which the movement is detected, by displaying a graphical marker on the reconstructed MR image which is obtained via the pulse sequence in which the movement is detected, and
the method further comprises:
extracting the reconstructed MR image, which is obtained via the pulse sequence in which the movement is detected, and
displaying the extracted reconstructed MR image on the screen.

24. The method of claim 23, wherein the graphical marker is displayed when a value of a movement amount of the object is equal to or greater than a threshold value.

25. The method of claim 23, further comprising:
compensating another MR image, of the reconstructed MR images, that is obtained via the pulse sequence in which the movement is detected from the plurality of pulse sequences of the protocol, when a level of the movement is less than the threshold value.

26. The MRI apparatus of claim 25, further comprising displaying a marker indicating the another MR image which is compensated.

27. The method of claim 1, wherein the title of a corresponding pulse sequence, in which the movement is detected, is displayed together with the first graphical marker or the second graphical marker, respectively, in a same area of the screen in which the title is displayed.

28. The MRI apparatus of claim 17, wherein the graphical marker is displayed on the at least one of the reconstructed MR image, which is obtained via the pulse sequence in which the movement is detected.

29. The MRI apparatus of claim 9, further comprising:
a sensor configured to detect the movement of the object while the protocol is executed.

30. The MRI apparatus of claim 17, further comprising:
a sensor configured to detect the movement of the object while the protocol is executed.

31. The MRI apparatus of claim 17, wherein the reconstructed MR images, which are obtained via the plurality of pulse sequences, are displayed on the screen at the same time in a grid.

32. The MRI apparatus of claim 17, wherein respective reconstructed MR images are images which are displayed on the screen separately from one another in each corresponding area of the screen, respectively.

* * * * *